US012742154B2

(12) United States Patent
Rowat et al.

(10) Patent No.: US 12,742,154 B2
(45) Date of Patent: Sep. 22, 2026

(54) METHODS AND COMPOSITIONS FOR CELL CULTURE ON HETEROGENEOUS SCAFFOLDS

(71) Applicant: The Regents of the University of California, Oakland, CA (US)

(72) Inventors: Amy Rowat, Los Angeles, CA (US); Nora Stephanie Kawecki, Los Angeles, CA (US); Siobhan Ariel Braybrook, Los Angeles, CA (US); Sam Norris, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1007 days.

(21) Appl. No.: 17/604,840

(22) PCT Filed: Apr. 23, 2020

(86) PCT No.: PCT/US2020/029629

§ 371 (c)(1),
(2) Date: Oct. 19, 2021

(87) PCT Pub. No.: WO2020/219755

PCT Pub. Date: Oct. 29, 2020

(65) Prior Publication Data

US 2022/0195392 A1 Jun. 23, 2022

Related U.S. Application Data

(60) Provisional application No. 62/837,514, filed on Apr. 23, 2019.

(51) Int. Cl.
*C12N 5/077* (2010.01)
*A23J 3/22* (2006.01)

(52) U.S. Cl.
CPC ............ *C12N 5/0658* (2013.01); *A23J 3/227* (2013.01); *C12N 2513/00* (2013.01); *C12N 2531/00* (2013.01); *C12N 2533/74* (2013.01)

(58) Field of Classification Search
CPC .................................................... C12N 5/0658
See application file for complete search history.

(56) References Cited

U.S. PATENT DOCUMENTS

2008/0009064 A1* 1/2008 Ronfard ............... C12N 5/0075 435/402
2011/0293685 A1 12/2011 Kuo et al.
2014/0242125 A1 8/2014 Atala et al.
2015/0079238 A1* 3/2015 Marga ..................... A23P 10/20 426/577
2018/0216072 A1* 8/2018 Lock .................... C12N 5/0075

FOREIGN PATENT DOCUMENTS

WO WO 2018/227016 12/2018
WO WO 2020/095305 5/2020
WO WO 2020/123876 6/2020

OTHER PUBLICATIONS

Downing et al. Biophysical regulation of epigenetic state and cell reprogramming. Nature Materials 2013, 12:1154-1162. (Year: 2013).*
Schmid. The role of meat fat in the human diet. Critical Reviews in Food Science and Nutrition 2010, 51; 1:50-66. (Year: 2010).*
Patel et al. Bioactive Nanofibers: Synergistic Effects of Nanotopography and Chemical Signaling on Cell Guidance. Nano Letters 2007, 7;7:2122-2128. (Year: 2007).*
Shahini et al. Efficient and high yield isolation of myoblasts from skeletal muscle. Stem Cell Research 2018, 30:122-129. (Year: 2018).*
Chen, S. et al., "Engineering multi-layered skeletal muscle tissue by using 3D microgrooved collagen scaffolds", *Biomaterials*, vol. 73, pp. 23-31, Sep. 11, 2015.
Condé, N. "The perfect steak is clean meat's biggest hurdle. Here's the solution" *Wired UK*, https://www.wired.co.uk/article/clean-meat-plant-scaffolds, Mar. 2, 2019.
DiMaio, T. "How do you marble cultivated beef?" *The Good Food Institute*, https://gfi.org/blog/amy-rowat-cultivated-beef Nov. 27, 2019.
Dolgin, E. "Sizzling interest in lab-grown meat belies lack of basic research", *Nature, Nature Publishing Group*, vol. 566, No. 7743, pp. 161-162, Feb. 6, 2019.
Extended European Search Report issued in corresponding European Application No. 20796163.2, dated Dec. 22, 2022.
Tajima S. et al., "Preparation of EpH4 and 3T3L1 cells aggregates incorporating gelatin hydrogel microspheres for a cell condition improvement", *Regenerative Therapy*, vol. 6, pp. 90-99, https://www.ncbi.nim.nih.gov/pmc/articles/PMC6134911/pdf/main.pdf Jun. 1, 2017.
Abbott et al., "The Use of Silk as a Scaffold for Mature, Sustainable Unilocular Adipose 3D Tissue Engineered Systems" *Adv. Healthcare Mater*. 2016, 5, 1667-1677.
Alborzi et al., "Electrospinning of Sodium Alginate-Pectin Ultrafine Fibers" *Journal of food science* 2010, 75, C100-C107.
Bodiou et al., "Microcarriers for Upscaling Cultured Meat Production" *Front Nutr* 2020, 7, 10, 16 pages.

(Continued)

*Primary Examiner* — Christopher M Babic
*Assistant Examiner* — Jennifer S Spence
(74) *Attorney, Agent, or Firm* — NORTON ROSE FULBRIGHT US LLP

(57) ABSTRACT

Embodiments of the invention describe a cultured meat or food product with more desirable flavor and texture, as well as methods and compositions for producing the same. Certain embodiments are directed to methods of producing a stiffer, structured surfaces or scaffolds that mimic the extracellular matrix (ECM) and support the growth of myotubes that are interspersed with a scaffold component supporting fat cells (adipocytes) in vitro.

21 Claims, 3 Drawing Sheets

(56) References Cited

OTHER PUBLICATIONS

Choi et al., "The influence of electrospun aligned poly(ϵ-caprolactone)/collagen nanofiber meshes on the formation of self-aligned skeletal muscle myotubes" *Biomaterials* 2008, 29(19), 2899-2906.
Daher and Braybrook. "How to let go: pectin and plant cell adhesion" *Front. Plant Sci.* 2015, 6(523), 8 pages.
Griffin et al., "Accelerated wound healing by injectable microporous gel scaffolds assembled from annealed building blocks" *Nature Materials* 2015, 14,737-744.
International Search Report and Written Opinion issued on Corresponding PCT Application No. PCT/US2020/029629, dated Jul. 22, 2020.
Irvine et al., "Printing cell-laden gelatin constructs by free-form fabrication and enzymatic protein crosslinking" *Biomed Microdevices* 2015, 17: 16, 8 pages.
Kirn and Uyama. "Biocompatible Hydrogel Formation of Gelatin from Cold Water Fish via Enzymatic Networking" *Polymer Journal* 2007, vol. 39, No. 10, pp. 1040-1046.
Lee et al., "Effect of Hierarchical Scaffold Consisting of Aligned dECM Nanofibers and Poly(lactide-co-glycolide) Struts on the Orientation and Maturation of Human Muscle Progenitor Cells" *ACS Appl. Mater. Interfaces* 2019, 11, 43, 39449-39458.
Levesque-Tremblay et al., "Tuning of pectin methylesterification: consequences for cell wall biomechanics and development" *J Planta 2015*, 242, 791-811.
MacQueen et al., "Muscle tissue engineering in fibrous gelatin: implications for meat analogs" Science of Food 2019, 13 pages.
Ostrovidov et al., "Gelatin-Polyaniline Composite Nanofibers Enhanced Excitation-Contraction Coupling System Maturation in Myotubes" *ACS Appl. Mater. Interfaces* 2017, 9, 49, 42444-42458.
Ostrovidov et al., "Myotube formation on gelatin nanofibers e Multi-walled carbon nanotubes hybrid scaffolds" *Biomaterials* 2014, 35, 6268-6277.
Qazi et al., "Biomaterials based strategies for skeletal muscle tissue engineering: Existing technologies and future trends" *Biomaterials* 2015, 53, 502-521.
Ricotti et al., "Proliferation and skeletal myotube formation capability of C2C12 and H9c2 cells on isotropic and anisotropic electrospun nanofibrous PHB scaffolds" Biomedical materials 2012, 7, 035010.
Verbruggen et al., "Bovine myoblast cell production in a microcarriers-based system" *Cytotechnology* 2018, 70:503-512.
Yeo, Miji and Kim, GeunHyung. "Nano/microscale topographically designed alginate/PCL scaffolds for inducing myoblast alignment and myogenic differentiation" *Carbohydrate Polymers* 2019, 223, 115041.
Young et al., "Stimulation of adipogenesis of adult adipose-derived stem cells using substrates that mimic the stiffness of adipose tissue." *Biomaterials*. 2013; 34:8581-88.

* cited by examiner

METHODS AND COMPOSITIONS FOR CELL CULTURE ON HETEROGENEOUS SCAFFOLDS

CROSS-REFERENCE TO RELATED APPLICATIONS

This application is a national phase application under 35 U.S.C. § 371 of International Application No. PCT/US2020/029629, filed Apr. 23, 2020, which claims the benefit of priority of U.S. Provisional Patent Application No. 62/837,514, filed Apr. 23, 2019, both of which are hereby incorporated by reference in their entirety.

STATEMENT REGARDING FEDERALLY FUNDED RESEARCH

This invention was made with Government support under 1735325 awarded by the National Science Foundation. The Government has certain rights in the invention.

BACKGROUND

Certain embodiments are directed to the fields of cellular biology and food production. Certain aspects are directed to methods and composition related to producing a cultured food product.

Innovations in food production are urgently needed to feed the global population, which is projected to increase by nearly 30% to 9.8 billion in the next 30 years (World Population Prospects 2017, URL esa.un.org/unpd/wpp/, 2017; Godfray, et al. *Science,* 1185383, 2010; Godfray et al. *Science,* 361:5324, 2018). Meat is the primary source of proteins and many essential nutrients in developed economies (Speedy, *Global production and consumption of animal source foods.* 133:4048S-4053S, 2003; Pereira and Vicente, *Meat nutritional composition and nutritive role in the human diet.* 93:586-92, 2013). However, the production of meat is the largest consumer of environmental resources in the food industry (Steinfeld et al. *Food and Agriculture Org.,* 2006; Gerber et al. *Food and Agriculture Organization of the United Nations* (*FAO*), 2013). In particular, beef production requires the highest amounts of non-renewable energy, water, and land use, and also has the highest total greenhouse gas emissions (GHGE) of all foods (Steinfeld et al. *Food and Agriculture Org.,* 2006; Gerber et al. *Food and Agriculture Organization of the United Nations* (*FAO*), 2013; Schlink et al., *Rev. Sci. Tech* 29:603-19, 2010; *Food and Agriculture Organization of the United Nations FAO*, Rome 2009; Opio et al. Greenhouse gas emissions from ruminant supply chains—A global life cycle assessment. 1-214, 2013; Wirsenius et al., Climate Impact of Food and Agriculture. Chapter in The Meat Crisis: Developing More Sustainable and Ethical Production and Consumption, 2017).

The average individual in the U.S. eats upwards of 54 pounds of beef annually (Food and Agriculture Organization of the United Nations FAO, Rome 2009; Davis et al., U.S. Dept of Agriculture, Economic Research Service, 2018; Roser, Meat and seafood production & consumption, URL ourworldindata.org/meat-and-seafood-production-consumption, 2018), which is equivalent to nearly 4 times the gallons of freshwater and 0.5 times the $CO_2$ emissions from automobile use for the average American per year (Perlman, URL water.usgs.gov/edu/qa-home-percapita.html, 2016; URL epa.gov/greenvehicles/greenhouse-gas-emissions-typical-passengervehicle, 2018). The conversion of plant energy to consumable beef calories is poor (1.9%) compared to other animals (13% for poultry) (Roser, URL ourworldindata.org/meat-and-seafood-production-consumption, 2018), as the majority of energy is lost due to cattle metabolism and manure (Nkrumah, J. et al. *Journal of animal science* 84:145-53, 2006). Climate change poses an additional challenge in shifting the potential of land used for livestock agriculture due to global warming, rising sea levels, more frequent droughts and reductions in water availability (Schmidhuber and Tubiello, *PNAS* 104:19703-08, 2007; Olesen and Bindi, *European journal of agronomy* 16:239-62, 2002). Strategies have been proposed to reduce the environmental impact of beef, such as changing cattle diet (Hulshof et al. *Journal of Animal Science* 90:2317-23, 2012) and treating manure to reduce GHGE (Masséet al., *Animal feed science and technology* 166: 436-45, 2011). But if a small reduction in the amount of beef consumed by individuals can be achieved, this would have major impact on energy, water, land use, and GHGE (Hedenus et al., *Climatic Change.* 124:79-91, 2014; Bajzželj et al. *Nature Climate Change.* 4:924, 2014; Bryngelsson et al., *Food Policy* 59:152-164, 2016; Springmann et al., *PNAS.* 113:4146-51, 2016; Berners-Lee et al., *J Elem Sci Anth.* 6, 2018; Cleveland and Gee, in Vegetarian and Plant-Based Diets in Health and Disease Prevention 135-156, Elsevier, 2017).

However, eating behaviors are hard to change (Mann et al., *American Psychologist* 62, 220, 2007). Humans have an intrinsic drive to eat energy-dense, nutrient-rich foods (King, *J American Psychologist.* 68:88, 2013). Meat is also a rich component of cultural traditions (MacInnis and Hodson, *Group Processes & Intergroup Relations* 20:721-44, 2017; Axelson, *Annual Review of Nutrition,* 6:345-63, 1986), and its relative low cost and ready availability further drive meat consumption (Kearney, *J Phil. Trans. Royal Soc. London B: Biological Sciences.* 365:2793-2807, 2010). A nationally representative poll shows over 95% of Americans eat meat (Davis and Lin, U.S. Dept of Agriculture, Economic Research Service, 2018; Reinhart, URL news.gallup.com/poll/238328/snapshot-few-americans-vegetarian-vegan.aspx, 2018), and U.S. consumers are among the highest per capita consumers of beef in the world (Roser, URL ourworldindata.org/meat-and-seafood-production-consumption, 2018). While a small fraction of people are motivated to change their diet based on environmental, health, and animal welfare concerns (Mullee et al. *J. Appetite.* 114:299-305, 2017; Tuso et al., *The Permanente Journal.* 19:62, 2015; De Backer and Hudders, *J Ecology of food nutrition.* 53:639-57, 2014), significant reductions in beef production could be achieved by decreasing consumption among omnivores.

Informational strategies such as Meatless Mondays have raised awareness about the environmental and health benefits (Morris et al., *J International Journal of Sociology of Agriculture Food.* 21:189-208, 2014) of plant-based diets and have achieved modest reductions in meat consumption (URL mondaycampaigns.org/campaigns/meatless-monday/, 2013); however, the majority of consumers do not change their meat-eating behaviors (Verbeke et al., *J. Meat Sci.* 84:284-92, 2010). Thus, a promising approach to reduce beef consumption is to introduce desirable alternatives to beef in the diets of omnivores. The rapid rise of alternative protein sources. Plant-based meat mimics have been consumed for centuries in Buddhist cultures (Erway, URL tastecooking.com/buddhistmock-meats-paradox/, 2018; Krishna, URL atlasobscura.com/articles/where-to-buy-mockmeat?mc_cid=a755ea166c&mc_eid=5f5015d4ec, 2018), and have been commercially available (e.g. Tofurkey) for decades in the U.S. (Smith, URL smithsonianmag.com/artsculture/history-veggie-burger-180950163/, 2014; URL tofurky.com/our-story/our-roots/, 2018). But there is recent explosive growth in the plant-based meat industry, which is projected to reach $5 billion by 2020 (URL plantbasedfoods.org/consumeraccess/nielsen-data-release-2018/, 2018). In contrast to previous meat substitutes that use gluten (Aziz and Sanders, *J Proceedings of the Nutrition Society.* 71, 576-80, 2012) or bean blends, emerging plant-based products aim to recapitulate the texture, flavor, and color of beef, for example by using beet or genetically engineered heme proteins (Eisen, URL medium.com/impossible-foods/how-gmos-can-save-civilization-and-probably-already-have-6e6366cb893, 2018). While this generation of plant-based meat products achieves environmental benefits (Davis et al., *J Food Research International.* 43:1874-84, 2010; URL ift.org/~/media/Food%20Technology/Weekly/IF_SustainabilityReport2017.pdf, 2017), there is an unmet need for products that have the desirable sensory properties of meat (Hartmann and Siegrist, *Trends in Food Science & Technology* 61:11-25, 2017; Hoek et al. *Appetite* 56:662-73, 2011) and beef consumption continues to be on the rise (Godfray et al., *Science.* 361:5324, 2018).

Growing muscle from cells ex vivo is a promising approach to produce 'clean' or cultured meat: precursor muscle cells (myocytes) are harvested from animals and grown into skeletal muscle tissue (beef) in a bioreactor (Post, URL ecommons.cornelLedu/handle/1813/53370, 2017). Cultured meat products are under development and projected to come to market by 2021 (Bunge, URL wsj.com/articles/startup-producing-cell-grown-meat-raises-new-funding-1531738800? mod=searchresults&page=1&pos=1, 2018). Such an approach to produce beef has the potential to achieve significant environmental benefits (Tuomisto and Teixeira de Mattos, *Environmental science & technology* 45:6117-23, 2011) including up to 45% reductions in energy, 96% reductions in water, 99% reductions in land use, and 96% reductions in GHGE: the estimated yield from a 1,250 $m^3$ bioreactor (half the size of an Olympic swimming pool) is 3 million quarter pounders per year (Leber, URL fastcompany.com/3055504/when-will-our-meat-filled-diets-go-post-animal, 2016); while the cells to propagate this volume of cultured beef can be extracted from 1 living cow (URL mosameat.com/technology/, 2018), the equivalent amount produced by conventional methods would require 3,000 cows on 6.6 million $m^2$ of land over three years (URL nrcs.usda.gov/Internet/FSE_DOCUMENTS/stelprdb1097070.pdf, 2009). Existing cultured meat approaches rely on culturing a single cell type (myocytes) on the surfaces of polystyrene beads in bioreactors, and blending the cells into a unified meat product (Verbruggen et al., 70:503-512, 2018); Post, *Journal of the Science of Food Agriculture.* 94:1039-41, 2014; Bunge, URL wsj.com/articles/sizzling-steaks-may-soon-be-lab-grown-1454302862, 2016; Watson, URL foodnavigator-usa.com/Article/2017/12/21/Finless-Foods-co-founder-talks-clean-meat-clean-fish-cultured-meat, 2017). But the interspersing of fat within the muscle—aka 'marbling'—is critical for desirable flavor and texture of beef (Wood et al. *Proceedings of the nutrition society* 58, 363-70, 1999; Nishimura et al., *Journal of Animal Science.* 77, 93-104, 1999; Savell et al., *J. Food Sci.* 52, 517-19, 1987; Tuma et al. 21, 848-851, 1962). For example, the highly prized Wagyu beef has a high level of marbling (20-25% weight/mass)(Sturdivant et al., *J. Meat Sci.* 32, 449-58, 1992), making it one of the most flavorful and tender types of beef in the world (Nishimura et al., *Journal of Animal Science.* 77, 93-104, 1999; Andrien, URL ink.library.smu.edu.sg/ami/30, 2014). Moreover, existing methods produce cultured meat from precursor myocytes, and skeletal muscle is composed of myotubes.

There remains a need for additional methods and composition for producing a cultured meat product with more desirable flavor and texture.

SUMMARY

Embodiments of the invention describe a cultured meat or food product, as well as methods and compositions for producing the same. In certain aspects the meat or food product can have a more desirable flavor and texture. Certain embodiments are directed to methods of producing stiffer, structured surfaces or scaffolds that mimic the extracellular matrix (ECM) and support the growth of myotubes that are interspersed with a scaffold component supporting fat cells (adipocytes) in vitro.

Certain embodiments are directed to a product, food product, cultured food product, synthetic meat, edible artificial meat, meat substitute, or edible heterogeneous scaffold comprising a heterogeneous scaffold supporting growth and/or differentiation of multiple cell types, for example myocytes and adipocytes, forming a three dimensional food product. In certain aspects the heterogeneous scaffold has a first scaffold that can be nanofiber component and a second scaffold component that is less stiff than the first scaffold component, for example a component of aggregated microgels or microporous aggregate particles component. In certain aspects, the first scaffold can have a stiffness in the range of 0.5 to 1.0 MPa and a second, less stiff, scaffold component can have a stiffness of 0.5 to 2.5 KPa. In certain aspects, the first scaffold or nanofiber component can be an aligned nanofiber or a textured (e.g., micron-scale grooves) microcarrier component. The term "microcarrier" means a particulate material, such as a bead, gel, sphere, or other three dimensional shape. The purpose of using a particulate material is to expand the available surface area to a three dimensional structure for the cells to expand and grow. The nanofiber can be a functionalized and/or crosslinked nanofiber. The functionalized nanofiber can be a RGD functionalized nanofiber. In certain aspects, nanofibers or scaffold can be crosslinked using the transglutaminase enzyme. In certain aspects, nanofibers have a diameter of 150 to 400 nm. In certain instances the nanofibers can beat least, at most, or about 0.5, 1.0, 2.0, 3.0, 4.0, 5.0, 6.0, 7.0, 8.0, 9.0, 10, 15, 20, 25, 30, 35, 40, 45, or 50 cm, including all values and ranges there between. The nanofibers can comprise one or more of pectin, alginate, agarose, elastin, chitin, chitosan, fibrin, fibrinogen, polysaccharides, alginates, collagen, gelatin, poly(amino acids), peptides, polypeptides, poly($\alpha$-hydroxyacids), polylactic or polyglycolic acids, poly-lactide polyglycolide copolymers, poly-lactide polyethylene glycol (PEG) copolymers, polyesters, poly($\varepsilon$-caprolactone), poly(3-hydroxy-butyrate), poly(s-caproic acid), poly(p-dioxanone), poly(propylene fumarate), poly(ortho esters), polyol/diketene acetal addition polymers, polyanhydrides, poly(sebacic anhydride) (PSA), poly(carboxybiscarboxyphenoxyphenoxyhexane) (PCPP), poly[bis(p-carboxyphenoxy)methane] (PCPM), copolymers of SA, CPP and CPM poly (amino acids), poly(pseudo amino acids), polyphosphazenes, derivatives of poly[(dichloro)phosphazene], poly[(organo)phosph-azenes]polymers, polyphosphates, polyethylene glycol polypropylene block co-polymers, co-polymers prepared from the monomers of these polymers, random blends of these polymers, or mixtures and combinations thereof. In a further aspect the gelatin is crosslinked, for example, the gelatin is crosslinked by the enzyme transglutaminase. Other cross-linkers include EDC (1-Ethyl-3-[3-dimethylaminopropyl]carbodiimide hydrochloride)/NHS (N-hydroxysuccinimide) as a crosslinker. In certain aspects, the nanofiber is gelatin or crosslinked gelatin, pectin, alginate, agarose, or mixtures thereof.

In certain embodiments the myocyte is a mammalian, avian, or fish myocyte. In certain aspects a plant or yeast cell, which can be a myocyte substitute or in addition to a myocyte or myocyte substitute, can be cultured on the nanofiber component (i.e., first scaffold or myocyte microcarrier scaffold). The mammalian myocyte or myocyte substitute can be cow, pig, sheep, rabbit, fish, goat, deer, elk, or bison myocyte, or a soy cell. In certain embodiments the adipocyte, adipocyte precursor, adipocyte substitute is a mammalian, avian, or fish adipocyte or adipocyte precursor, or a plant or yeast cell, and can be cultured on a secondary scaffold or adipocyte microcarrier scaffold. The myocytes and the myocyte associated scaffold can be mixed or contacted with the adipocytes and the adipocyte associated scaffold before, during, and/or after culture to form a food product. The mammalian adipocyte or adipocyte precursor can be cow, pig, sheep, rabbit, fish, goat, deer, elk, or bison adipocyte or adipocyte precursor. In certain aspects an adipocyte substitute is an avocado cell. In certain aspects, the myocyte is from the same species as the adipocyte or adipocyte precursor. In other aspects, the myocyte is from a different species than the adipocyte or adipocyte precursor. In certain embodiments the ratio of myocytes to adipocytes is 10:1, 9:1, 8:1, 7:1, 6:1, 5:1, 4:1, 3:1 2:1 to 1:1, including all ratios and ranges there between. The average thickness of the food product can be between 0.5, 1, 2, 3, 4, 5, 6, 7, 8, 9, 10, 15, 20, 25, to 30 cm, including all values and ranges there between. The food product can contain 5, 10, 15, 20, 25, 30, 35, 40, 45, 50, 55, 60, 65, 70, 75, to 80 dry weight percent myotubes, myocytes, or myocyte substitute including the first scaffold component. The term "dry weight percent" as used herein means the weight of the designated components of a composition excluding any water that is present. The food product can contain 0.5, 1, 2, 3, 4, 5, 6, 7, 8, 9, 10, 11, 12, 13, 14, 15, 16, 17, 18, 19, 20, 25, 30, 35, 40, 45, 50, 60, 70, to 80 dry weight percent adipocytes or adipocyte substitute including the second scaffold components. In certain aspects a food product can be 10 to 20% dry weight myotubes, myocytes, or myocyte substitute including the first scaffold component and 10 to 60% dry weight adipocytes or adipocyte substitute including the second scaffold components. In certain aspects the food product can be 10, 20, 30, 40, 50, 60, 70, 80, to 90% water. The food product can further comprise additional nutritional components. In certain aspects the additional nutritional components are vitamins, minerals, polysaccharides, lipids, proteins, polypeptides, peptides, of dietary fiber. In particular aspects, the food product or food product components can be engineered (e.g., genetically engineered) to specifically exclude or produce reduced levels of selected components, such as saturated fats. In other aspects, the cultured cells can be engineered to produce heterologous food molecules or designed levels of food molecules.

Certain embodiments are directed to processes for producing, growing, manufacturing, or developing a cultured food product comprising at least the steps of: (i) culturing myocytes, myocyte precursors, or myocyte substitutes on a nanofiber substrate forming a myocyte-nanofiber complex or on a myocyte microcarrier scaffold forming a myocyte-microcarrier complex; (ii) culturing adipocytes, adipocyte precursors, or adipocyte substitutes on a microporous scaffold substrate forming an adipocyte-microporous scaffold complex or on an adipocyte microcarrier scaffold forming an adipocyte-microcarrier complex; (iii) optionally, (a) combining the myocyte-nanofiber complex and the adipocyte-microporous scaffold complex forming an integrated food precursor, or (b) culturing the myocyte-microcarrier complex and the adipocyte-microcarrier complex separately or together; and (iv) optionally, (a) culturing the integrated food precursor to form an cultured food product or (b) forming separately cultured myocyte microcarrier complexes and adipocyte carrier complex into a food product.

In certain aspects the nanofiber component is an aligned nanofiber component or a textured microcarrier scaffold comprised of nanofibers. The nanofiber can comprise pectin, alginate, agarose, elastin, chitin, chitosan, fibrin, fibrinogen, polysaccharides, alginates, collagen, gelatin or crosslinked gelatin, poly(amino acids), peptides, polypeptides, poly(α-hydroxyacids), polylactic or polyglycolic acids, poly-lactide poly-glycolide copolymers, poly-lactide polyethylene glycol (PEG) copolymers, polyesters, poly(ε-caprolactone), poly (3-hydroxy-butyrate), poly(s-caproic acid), poly(p-dioxanone), poly(propylene fumarate), poly(ortho esters), polyol/diketene acetal addition polymers, polyanhydrides, poly(sebacic anhydride) (PSA), poly(carboxybiscarboxyphenoxyphenoxyhexane) (PCPP), poly[bis(p-carboxyphenoxy)methane] (PCPM), copolymers of SA, CPP and CPM poly (amino acids), poly(pseudo amino acids), polyphosphazenes, derivatives of poly[(dichloro)phosphazene], poly [(organo)phosph-azenes]polymers, polyphosphates, polyethylene glycol polypropylene block co-polymers, co-polymers prepared from the monomers of these polymers, random blends of these polymers, or mixtures and combinations thereof. In particular aspects the nanofiber comprises gelatin, crosslinked gelatin, pectin, alginate, agarose, or mixtures thereof. In certain aspects, the myocyte is a mammalian, avian, fish myocyte or a plant or yeast cell. The mammalian myocyte can be cow, pig, sheep, rabbit, fish, goat, deer, elk, or bison myocyte, or a myocyte substitute such as a soy cell.

In certain embodiments the adipocyte, adipocyte precursor is a mammalian, avian, or fish adipocyte or adipocyte precursor, or the adipocyte substitute is a plant (e.g., avocado cell) or yeast cell. The mammalian adipocyte or adipocyte precursor can be cow, pig, sheep, rabbit, fish, goat, deer, elk, or bison adipocyte or adipocyte precursor. In certain aspects an adipocyte substitute is an avocado cell. In certain aspects, the myocyte is from the same species as the adipocyte or adipocyte precursor. In other aspects, the myocyte is from a different species than the adipocyte or adipocyte precursor.

Other embodiments are directed to processes for producing a cultured food product comprising at least the steps of: (i) forming a heterogeneous scaffold comprising a myocyte support and an adipose support; (ii) culturing myocytes, myocyte precursors, or myocyte substitutes in combination with adipocytes, adipocyte precursors, or adipocyte substitutes on the heterogeneous scaffold forming a cultured food product. Other methods include, but are not limited to the following: methods for preparing an edible composition, for manufacturing cultured myocytes for consumption, for manufacturing cultured adipocytes for consumption, for manufacturing cultured food products and the like.

Certain embodiments are directed to processes for producing a cultured food product comprising at least the steps of: (i) culturing myocytes, myocyte precursors, or myocyte substitutes on a first microcarrier scaffold (myocyte microcarrier scaffold) and culturing adipocytes, adipocyte precursors, or adipocyte substitutes on a second microcarrier scaffold (adipocyte microcarrier scaffold); (ii) forming a heterogeneous scaffold comprising cultured myocyte microcarrier scaffolds (forming a myocyte component) and an cultured adipocyte microcarrier scaffold (forming a adipocyte component) to produce a cultured food product.

In certain aspects the nanofiber component is an aligned nanofiber component or a textured microcarrier scaffold or non-textured microcarrier scaffold. The nanofiber can comprise pectin, alginate, agarose, elastin, chitin, chitosan, fibrin, fibrinogen, polysaccharides, alginates, collagen, gelatin, crosslinked gelatin, poly(amino acids), peptides, polypeptides, poly($\alpha$-hydroxyacids), polylactic or polyglycolic acids, poly-lactide poly-glycolide copolymers, poly-lactide polyethylene glycol (PEG) copolymers, polyesters, poly($\varepsilon$-caprolactone), poly(3-hydroxy-butyrate), poly(s-caproic acid), poly(p-dioxanone), poly(propylene fumarate), poly (ortho esters), polyol/diketene acetal addition polymers, polyanhydrides, poly(sebacic anhydride) (PSA), poly(carboxybiscarboxyphenoxyphenoxyhexane) (PCPP), poly[bis (p-carboxyphenoxy)methane] (PCPM), copolymers of SA, CPP and CPM poly (amino acids), poly(pseudo amino acids), polyphosphazenes, derivatives of poly[(dichloro) phosphazene], poly[(organo)phosph-azenes]polymers, polyphosphates, polyethylene glycol polypropylene block co-polymers, co-polymers prepared from the monomers of these polymers, random blends of these polymers, or mixtures and combinations thereof. In particular aspects the nanofiber or microcarrier comprises gelatin, crosslinked gelatin, pectin, alginate, agarose, or mixtures thereof. In certain aspects, the myocyte is a mammalian, avian, fish myocyte or a plant or yeast cell. The mammalian myocyte can be cow, pig, sheep, rabbit, fish, goat, deer, elk, or bison myocyte, or the myocyte substitute can be a soy cell. In certain embodiments the adipocyte, adipocyte precursor, adipocyte substitute is a mammalian, avian, or fish adipocyte or adipocyte precursor, or an plant or yeast cell. The mammalian adipocyte or adipocyte precursor can be cow, pig, sheep, rabbit, fish, goat, deer, elk, or bison adipocyte or adipocyte precursor. In certain aspects an adipocyte substitute is an avocado cell. In certain aspects, the myocyte is from the same species as the adipocyte or adipocyte precursor. In other aspects, the myocyte is from a different species than the adipocyte or adipocyte precursor.

The term "food product" is used herein to refer generally, according to context, to an actual consumable food item or to cultured meat food item that is edible or fit for consumption by an animal without substantial short term and/or long term adverse effects.

The term "food molecule" is used herein to refer generally, according to context, to a molecule that can be consumed and assimilated or used by an animal as a source of calories, nutrition, or molecules to be assimilated or used in the physiology of the animal.

The term "fibrous scaffold" refers herein to a three dimensional structure formed by oriented fibers. In some embodiments, electrospinning methods are used to achieve the oriented fiber construction.

As used herein, "scaffold" refers to a structure, comprising a biocompatible material that provides a surface suitable for adherence and proliferation of cells. A scaffold may further provide mechanical stability and support. A scaffold may be in a particular shape or form so as to influence or delimit a three-dimensional shape or form assumed by a population of proliferating cells. Such shapes or forms include, but are not limited to, films (e.g. a form with two-dimensions substantially greater than the third dimension), ribbons, cords, sheets, flat discs, cylinders, spheres, 3-dimensional amorphous shapes, etc. In certain aspects the scaffold can be a heterogeneous scaffold having at least two distinct characteristics independently distributed through the scaffold structure.

The terms "cells" and "population of cells" are used interchangeably and refer to a plurality of cells, i.e., more than one cell. The population may be a pure population comprising one cell type. Alternatively, the population may comprise more than one cell type. In the present invention, there is no limit on the number of cell types that a cell population may comprise.

"Muscle cells" or "myocytes" include those cells normally found in muscle tissue, including smooth muscle cells, cardiac muscle cells, skeletal muscle cells, and any combination thereof.

"Myocyte substitute" include cells that can differentiate into myocytes or muscle tissue under the appropriate conditions.

As used herein, the term "myotube" refers to muscle fibers that are generally formed through the fusion of myoblasts into multi-nucleated fibers.

The term "preadipocyte" refers to a cell existing in or isolated from fat tissue which is capable of replicating yet is committed to the adipogenic phenotype (i.e., is committed to differentiate into an adipocyte or fat cell). In their undifferentiated state, cultured preadipocytes resemble fibroblasts (i.e., have a fibroblast-like morphology). In particular, they exhibit a flattened, adherent morphology and contain very little microscopically-detectable lipid.

The term "adipocyte" refers to a cell existing in or derived from fat tissue which is terminally differentiated. In their differentiated state, adipocytes assume a rounded morphology associated with cytoskeletal changes and loss of mobility. They further accumulate lipid as multiple small vesicles that later coalesce into a single, large lipid droplet displacing the nucleus.

Throughout this application, the term "about" is used to indicate that a value includes the inherent variation of error for the device, the method being employed to determine the value, or the variation that exists among the study subjects.

The terms "comprise," "have," and "include" are open-ended linking verbs. Any forms or tenses of one or more of these verbs, such as "comprises," "comprising," "has," "having," "includes," and "including," are also open-ended. For example, any method that "comprises," "has," or "includes" one or more steps is not limited to possessing only those one or more steps and also covers other unlisted steps.

The use of the term "or" in the claims is used to mean "and/or" unless explicitly indicated to refer to alternatives only or the alternatives are mutually exclusive, although the disclosure supports a definition that refers to only alternatives and "and/or."

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating embodiments of the invention, are given by way of illustration only, since various changes and modifications within the spirit and scope of the invention will become apparent to those skilled in the art from this detailed description.

It is contemplated that embodiments described in the context of the term "comprising" may also be implemented in the context of the term "consisting of" or "consisting essentially of."

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention. Use of the one or more compositions may be employed based on methods described herein. Use of one or more compositions may be employed in the preparation of medicaments for treatments according to the methods described herein. Other embodiments are discussed throughout this application. The embodiments in the Example section are understood to be embodiments that are applicable to all aspects of the technology described herein.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DETAILED DESCRIPTION

Methods described herein are directed to the generation of scaffolds that support the growth of myocytes and adipocytes. Studies show (1) Aligned scaffolds promote differentiation of myocytes into myotubes; (2) Microcarrier scaffolds with tunable mechanics and topology; (3) Scaffolds that promote fat production by adipocytes; (4) Media formulation that supports both myotubes and adipocytes; and (5) Composite scaffolds with myotubes and adipocytes.

Figures 3A, 3B, 3C, 3D, 3E:
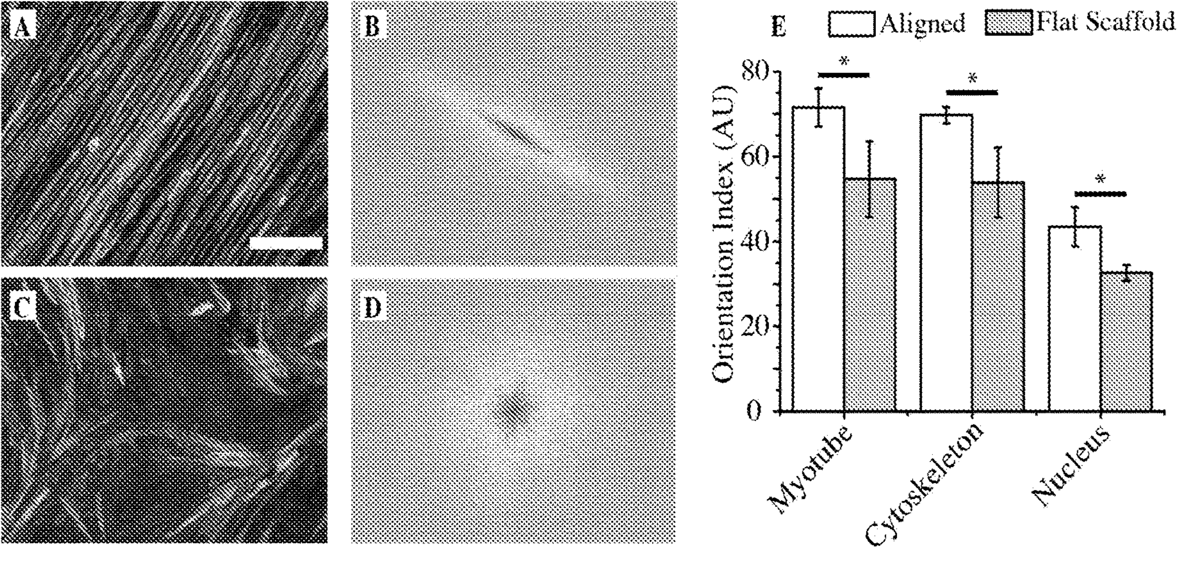
FIG. 3A-3E. Aligned scaffolds for myocyte differentiation. C2C12 mouse myocytes are cultured on transglutaminase-crosslinked 10 wt % gelatin scaffolds with (A.) grooved topology or (C.) a flat surface. Grooved topology (10 μm wide, 3 μm deep channels) is achieved using microfabrication and soft lithography. After 8 days of culturing myocytes on 10 wt % gelatin hydrogels (21 kPa), myocytes show high degree of alignment and characteristics of myotubes when cultured on grooved versus flat substrates. Green: Actin (Phalloidin), Red: Myosin, Blue: nucleus (DAPI). Scale, 200 μm. Alignment of cells on (B.) grooved topology and (D.) flat surface is quantified using a 2D Fourier transform; a higher "Orientation Index" (Chaudhuri et al., *IEEE Trans Biomed Eng* 34, 509-518, 1987) indicates more alignment. (E.) The Orientation Index determined using three separate fluorescent channels (myosin heavy chain, phalloidin, DAPI). *: $P<0.05$; student t-test.

Aligned scaffolds promote differentiation of myocytes into myotubes. Previous findings demonstrated that aligned nanofibers can promote the differentiation of myocytes into multinucleated myotubes, which are the precursors of muscle fibers (Ostrovidov et al., *Biomaterials* 35, 6268-6277, 2014; Qazi et al., *Biomaterials* 53, 502-521, 2015; Yeo and Kim, *Carbohydr Polym* 223, 115041, 2019; Lee et al., *ACS Appl Mater Interfaces* 11, 39449-39458, 2019). With expertise in microfabrication (Schmitz et al., 2009; Gill et al., *Lab on a Chip* 19, 343-357, 2019; Rowat et al., *Proc Natl Acad Sci USA* 106, 18149-18154, 2009), the inventors have generated aligned structures that promote the differentiation of myocytes into myotubes (FIG. 3); this is one approach for generating muscle in vitro. The topology of these structured scaffolds can be controlled using soft lithography to produce patterns with down to ~1 μm resolution. However, the production of cultured meat requires scaffolds with aligned topology that can be scaled up and withstand the physical stresses of culture in a bioreactor.

Microcarrier scaffolds with tunable mechanics and topology. To achieve cultured meat production at scale, anchorage-dependent cells can be cultured in a bioreactor on the surface of microcarriers; this provides myoblasts with a solid surface to which they can attach and maximizes surface area. Current efforts to produce cultured meat are exploring varying types of microcarrier materials, including synthetic polymers (Verbruggen et al., *Cytotechnology* 70, 503-512, 2018), which would require the removal of muscle cells from the beads prior to harvesting. However, the development of edible microcarrier scaffolds could allow for an increase in production efficiency. In addition, current limitations to upscaling cell culture on microcarriers arise given the varying growth conditions needed during cell proliferation versus differentiation phases (Bodiou et al., *Front Nutr* 7, 10, 2020). Thus, the ideal microcarrier design would be edible and provide the proper mechanical environment to allow for both the proliferation and differentiation of muscle cells in a single-batch bioreactor system. Preliminary data show the generation of food-grade microcarriers with aligned topologies that promote myotube differentiation, microcarrier scaffolds have been made with 750 μm diameter and grooves with 10 μm spacing. Using microfabrication processes, the size, aspect ratio, topology, and mechanics of microcarrier particles can be fine-tuned. When myocytes are seeded on these microcarrier scaffolds with aligned topology, they form similar aligned patterns on the microcarriers as on the bulk substrate; they also proliferate and differentiate to form myotubes in a single-batch bioreactor system. Importantly, this enables scaled-up culture in a bioreactor setting.

Scaffolds that promote fat production by adipocytes. Fat cells or adipocytes are another key component for the sensory properties of cultured meat (Fish et al., *Trends Food Sci Technol* 98, 53-67, 2020). High lipid density, and more specifically high polyunsaturated phospholipid concentration, increases the concentration of aromatic compounds and reduces the volatility of flavor compounds (Legako et al.,

*Meat Sci* 100, 291-300, 2015; Elmore et al., *J Agric Food Chem* 47, 1619-1625, 1999; Rabe et al., *J Sci Food Agr* 83, 1124-1133, 2003). Mesenchymal stem cells differentiation into adipocytes had been shown to occur on softer materials (elastic modulus, E~1 kPa)(Young et al., *Biomaterials* 34, 8581-8588, 2013). To determine how scaffold mechanics determines the amount of lipids produced by adipocytes, the inventors tested the growth, differentiation, and fat production of adipocytes on scaffolds of varying stiffness and composition. Data shows that adipocytes have robust adhesion to collagen-coated scaffolds with 2 kPa stiffness, rather than stiffer scaffolds (E~15 kPa); importantly, adipocytes on 2 kPa scaffolds show robust lipid production.

Media formulation that supports both myotubes and adipocytes. Another challenge of co-culture of different cell types is the media formulation: different cell types may require specific media formulations to promote their growth. Specifically, myocytes require media that contains 2% serum, while adipocyte fat production has been shown to require high serum conditions (20%) for differentiation (Madsen et al., *Biochem J* 375, 539-549, 2003; Yaffe and Saxel, *Differentiation* 7, 159-166, 1977). To allow for simultaneous culture of both cell types, the inventors have developed an approach to co-culture muscle and fat cells post-differentiation. Findings show that varying the ratio of muscle to fat media has no major effects on differentiation markers in both muscle and fat cells.

Composite scaffolds with myotubes and adipocytes. Achieving marbled cultured meat requires tuning the ratio of myotubes to adipocytes, as well as the size of adipocyte clusters to control the spatial distribution of marbling. The inventors have developed a unique approach to tune the size of adipocyte-scaffold-clusters and formulate marbled scaffolds: spherical gelatin microcarrier scaffolds were produced, which the adipocytes can adhere to, and mix these spherical microcarriers-laden-with-adipocytes with the myotube scaffolds. Given the inherent propensity of cells to adhere to nearby surfaces, this drives the self-assembly of myotube and adipocyte scaffolds, as adipocytes on beads bind to each other, as well as to nearby beads; this enables one to tune the size of 3D aggregate scaffolds prior to integration into the myotube scaffold system. After injection, adipocytes adhere to myotubes to form a unified, composite material.

Microcarrier scaffolds with tunable mechanics and topology were generated to optimize two essential components of cultured meat: (1) muscle fibers that derive from precursor myocytes; and (2) the composition of intramuscular fat that derives from adipocytes. Using microfabrication and cell biology, the inventors can determine the optimal composition and structure of scaffolds while also ensuring minimal environmental impact. These novel scaffolds can be used as building blocks to generate marbled cultured meat that contains both fully-differentiated muscle fibers and adipocytes, and assess the sensory and nutrient properties as a function of intramuscular fat composition.

Methods are described herein for development of microcarriers with tunable mechanics and topology that support the production of marbled cultured meat. Tuning textures of cultured meat with varying fat content significantly improves the sensory and nutrient properties of cultured meat.

Embodiments are directed to addressing the question of how can cultured meat or food product containing myocytes or myotubes be generated that is desirable to the public. Methods and compositions described herein can provide a favorable texture and flavor for cultured meat or food product while minimizing energy consumption, water consumption, land use, and greenhouse gas emissions (GHGE). Embodiments are directed to production of marbled cultured meat, e.g., beef, or food product that has desirable texture and flavor.

I. Cultured Meat and Production Thereof

Described herein are methods for producing cultured meat, e.g., marbled cultured meat. Certain embodiments will include methods and compositions having a reduced or minimal energy, water, land use, and minimal GHGE footprint. In certain aspects, scaffolds are engineered to support the growth and maturation of spatially patterned muscle and fat cells, e.g., heterogeneous scaffolds or produce formed of heterogeneous scaffolds.

The production of marbled cultured beef can provide an alternative for conventional beef production, which is a major consumer of environmental resources. More broadly, methods for growing cultured beef have potential to increase the resiliency and sustainability of food production as they can require significantly less energy, water, and land and are therefore less susceptible to increasing variability in climate. For example, cultured meat can be sustainably produced in regions where agricultural production is challenged, such as in urban centers, food deserts, and extreme environment including space.

In other aspects multiple cell types can be patterned into cohesive three-dimensional tissues, e.g., food products. In other aspects, methods and composition are defined to generate patterned materials with heterogeneous mechanical properties across a range of length scales.

A. Production of Marbled Cultured Meat

Embodiments are directed to methods for generating a marbled cultured meat that has desirable texture and flavor. In certain aspects the cultured meat can have a reduced or minimal environmental impact. The texture and flavor of meat contributes to palatability (Wood et al., *Proc. Nutr. Soc.* 58:363-70, 1999; Nishimura et al., *J. Animal Sci.* 77:93-104, 1999; Savell et al., *J. Food Sci.* 52, 517-19, 1987; Tuma et al., Influence of Marbling and Animal Age on Factors Associated with Beef Quality 1, 2, 3, 4. 21:848-51, 1962), which is a factor driving food choices (Pliner and Mann, *J. Appetite.* 42:227-37, 2004). However, myocytes require aligned structures of a specific stiffness in order to form mature myotubes, which comprise skeletal muscle and are important for meat texture (Post, URL ecommons.cornell.edu/handle/1813/53370, 2017). Myotube formation on a structured matrix of aligned nanofibers produced by electrospinning has been demonstrated (Ostrovidov et al., *J Appl. Mater. & Interfaces* 9:42444-58, 2017), the nanofibers having a stiffness that promotes the maturation of precursor myocytes into myotubes and thus muscle. Plant-based source ingredients for cultured meat can be used to minimize the reliance on animal products, and thus minimize environmental burden (Gershlak et al., *J. Biomaterials.* 125:13-22, 2017). Pectin and alginate polymers can be used as scaffolds that are mechanically tunable for cell-type specific growth by varying calcium ion concentration (Levesque-Tremblay et al., *J Planta* 242:791-811, 2015; Daher and Braybrook, *J Front. Plant Sci.* 6:523, 2015). A variety of other polymers may be used to generate a nanofiber scaffold of sufficient stiffness.

Cultured meat with mature myotubes may have improved texture compared to myocytes alone. Another major determinant of meat flavor and texture of meat is fat (Wood et al., *Proc. Nutri. Soc.* 58:363-70, 1999; Nishimura et al., *J Animal Sci.* 77:93-104, 1999; Savell et al., *J. Food Sci.* 52:517-19, 1987; Tuma et al., Influence of Marbling and Animal Age on Factors Associated with Beef Quality 1, 2, 3, 4. 21:848-51, 1962; Goodson et al., *J Animal Sci.* 80:401-08, 2002; Dashdorj et al., *J Euro. Food Res. Tech.* 241:157-71, 2015). Thus, the production of marbled cultured meat with both muscle and fat cells could significantly improve the texture and flavor. To meet the requirements for marbled cultured meat production, muscle cells (myocytes) and fat cells (pre-adipocytes) must be grown together and mature into myotubes and fat-producing adipocytes. However, myocytes prefer a stiffer, structured matrix (Qazi et al., *Biomaterials* 53:502-21, 2015), while adipocytes prefer a more deformable matrix (Young et al., *Biomaterials* 34:8581-88, 2013).

In one aspect, achieving cultured muscle tissue that has fat cells interspersed between myotubes, a convergent approach is used, generating stiffer nanofibrous scaffolds, e.g., by electrospinning, and a more deformable scaffold (a second scaffold component) that is preferable to adipocytes, e.g., a scaffold of microgel particles. In other aspects, muscle tissue and fact cells can be cultured on separate microcarriers and formed post-culture to produce a food product.

Microgels can be fabricated using droplets of a water-in-oil emulsion (Griffin et al., *Nature materials* 14:737-44, 2015) as templates for hydrogel particles; when cells are seeded on microgels, they adhere to other microgels and nearby cells to form a mechanically stable scaffold. By tuning the stiffness of the microgels to match the preference of adipocytes (~2 kPa) (Young et al., *Biomaterials* 34:8581-88, 2013), injecting the particles together with adipocytes into the interstitial gaps between nanofibers, a scaffold with heterogeneous stiffness can be generated that can support the maturation of both muscle and fat. The heterogeneous scaffold technology enables a unique and innovative strategy to build structured scaffolds that have tunable architecture, stiffness, and therefore the spatial organization of cells.

In a further aspect, generating stiffer nanofibrous scaffolds, e.g., by electrospinning, and a more deformable scaffold (a second scaffold component) that is preferable to adipocytes, e.g., using droplets of water-in-oil emulsions as templates for hydrogel particles (Nyberg et al., *Biophys J.* 113(7):1574-1584, 2017; Nyberg et al. (2016) Lab Chip. 16: 3330-3339). By tuning the stiffness of the microgels to match the preference of adipocytes (~2 kPa) (Young et al., *Biomaterials* 34:8581-88, 2013), injecting the particles together with adipocytes into the interstitial gaps between nanofibers, and then annealing, generates a scaffold with heterogeneous stiffness that can support the maturation of both muscle and fat. The heterogeneous scaffold technology enables a unique and innovative strategy to build structured scaffolds that have tunable architecture, stiffness, and therefore the spatial organization of cells.

By varying the ratio of fat to muscle in cultured meat, marbled cultured beef can be engineered to have similar texture, flavor, and nutritional profiles as natural meat or beef.

Marbled cultured meat that meets the taste, texture, and nutritional profiles of beef produced in vivo provides a sustainable and delicious alternative to beef production with reduced energy, water, land use, and GHGE. The methodology for generating materials with heterogeneous mechanical properties for co-culture of multiple cell types should be valuable for cultured meat production as well as in tissue engineering.

1. Structured Scaffold to Promote Myotube Formation

To form skeletal muscle from myocytes, a structured or textured scaffold is generated from one or more polymer. In certain aspects the polymers are plant-based polymers such as gelatin, pectin, and/or alginate. The generation of myotubes will result in improved texture of cultured meat over myocytes alone. The nanofibers can comprise or consist of one or more polymers. The polymer may comprise or consist of a biocompatible polymer. The polymer may comprise or consist of a digestible polymer. The polymer may comprise or consist of aliphatic polymer, biodegradable polyesters, or other biodegradable polymers. The polymer may be thermoplastic. The polymer may comprise or consist of any polymer selected from the group comprising gelatin or crosslinked gelatin, hydroxypropyl methylcellulose (HPMC), poly(α-hydroxyacids), polylactic or polyglycolic acids, poly-lactide poly-glycolide copolymers, poly-lactide polyethylene glycol (PEG) copolymers, polyesters, poly(ε-caprolactone), poly(3-hydroxy-butyrate), poly(s-caproic acid), poly(p-dioxanone), poly(propylene fumarate), poly (ortho esters), polyol/diketene acetal addition polymers, polyanhydrides, poly(sebacic anhydride) (PSA), poly(carboxybiscarboxyphenoxyphenoxyhexane) (PCPP), poly[bis (p-carboxyphenoxy)methane] (PCPM), copolymers of SA, CPP and CPM poly (amino acids), poly(pseudo amino acids), polyphosphazenes, derivatives of poly[(dichloro) phosphazene], poly[(organo)phosph-azenes]polymers, polyphosphates, polyethylene glycol polypropylene block co-polymers, natural polymers, silk, elastin, chitin, chitosan, fibrin, fibrinogen, polysaccharides (including pectins), alginates, collagen, poly(amino acids), peptides, polypeptides or proteins, whey protein(s), cellulose or cellulose blends, co-polymers prepared from the monomers of these polymers, random blends of these polymers or mixtures and combinations thereof. In certain embodiments the myotube nanofiber or scaffold can comprise pectin, alginate, or pectin and alginate. As used herein, a "pectin" is any one of a family of galacturonic acid-rich polysaccharides including homogalacturonan, rhamnogalacturonan I, and the substituted galacturonans rhamnogalacturonan II (RG-II) and xylogalacturonan (XGA), as described in Mohnen, "Pectin Structure and Biosynthesis," Current Opinions in Plant Biology, 11:266-277, 2008. High methoxyl pectins and amidated pectins are variations of the pectin family. One or more polymer can be independently present in an amount that is 0.5, 1.0, 1.5, 2.0, 2.5, 3.0, 3.5, 4.0, 4.5, 5.0, 5.5, 6.0, 6.5 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, 50.0, 50.5, 51.0, 51.5, 52.0, 52.5, 53.0, 53.5, 54.0, 54.5, 55.0, 55.5, 56.0, 56.5, 57.0, 57.5, 58.0, 58.5, 59.0, 59.5, 60.0, 60.5, 61.0, 61.5, 62.0, 62.5, 63.0, 63.5, 64.0, 64.5, 65.0, 65.5, 66.0, 66.5, 67.0, 67.5, 68.0, 68.5, 69.0, 69.5, 70.0, 70.5, 71.0, 71.5, 72.0, 72.5, 73.0, 73.5, 74.0, 74.5, 75.0, 75.5, 76.0, 76.5, 77.0, 77.5, 78.0, 78.5, 79.0, 79.5, 80.0, or 80.5 dry weight percent (w/w), including all values and ranges there between.

In certain embodiments, the heterogeneous scaffold comprises a first myocyte microcarrier scaffold. The myocyte microcarrier scaffold can have grooves, grooves having a length of 50 to 500 μm, depth of 1 to 50 μm and a width of 1 to 50 μm with a spacing between grooves of 1 to 50 μm. The myocyte microcarrier scaffold has a first dimension between 50 to 500 μm and a second dimension of 50 to 500 μm. In certain aspects, the myocyte microcarrier scaffold is spherical, ovoid, cylindrical, or egg shaped. In certain instances, the myocyte microcarrier scaffold has an average aspect ratio (long axis to short axis) ranging from 1, 2, 3, 4, 5, 6, 7, 8, 9, to 10 including all ratios and ranges there between. The myocyte microcarrier scaffolds and associate with each other to form aggregates during culture. The myocyte microcarrier can be molded using a two or three dimensional mold.

In other embodiments, the nanofiber scaffold component may comprise or consist of monofilaments or fibers. The fibers may be formed by spinning, such as electrospinning. The nanofiber scaffold component may comprise or consist of electrospun polymer. The monofilaments or fibers of the nanofiber scaffold component may be between about 150, 175, 200, 225, 250, 275, 300, 325, 350, 375, to about 400 nm in diameter, including all ranges and values there between. The monofilaments or fibers of the myotube component may be between about 150, 175, 200, 225, 250, 275 nm and about 300, 325, 350, 375, 400, 425, 450 nm in diameter, including all values and ranges there between. The fibers of the material layer may be substantially aligned. In certain aspects, substantially aligned refer to the long axis of the fibers being for most part parallel, but may deviate by an angle of 1, 2, 3, 4, 5, 6, 7, 8, 9, 10, 11, 12, 13, 14 15, 16, 17, 18, 19, 20, 21, 22, 23, 24, 25, 26, 27, 28, 29, or 30 degrees with respect to each other.

In certain embodiments, the nanofiber diameters can be tuned ranging from at least, at most, or about 20, 30, 40, 50, 60, 70, 80, 90, 100, 110, 12, 130, 140, 150, 160, 170, 180, 190 to 200 nm, including all values and ranges there between. The component ratio can be adjusted to tune the diameter, for example component (e.g., alginate/pectin) ratios (w/w) include, but are not limited to 80/20, 70/30, 60/40, 50/50. Certain aspects the nanofiber scaffold comprises gelatin or crosslinked gelatin, alginate/pectin blends (Alborzi et al., *Journal of food science* 75(1):C100-C107, 2010); whey protein isolate/cellulose blends (e.g., 1-2%/0.25-1% (Tam et al., *Food research international* 102:616-24, 2017); polysaccharide/PVA blends (e.g., 0.5-2%/15-5% respectively)(Santos et al., (2014) *Carbohydrate polymers* 99:584-92; Islam and Karim, (2010) *Colloids and Surfaces A: Physicochemical and Engineering Aspects* 366(1-3):135-140); Pectin/HPMC or PEO (e.g., 5%/5%)(Chen et al., (2018) *Biomacromolecules,* 19(2):490-98); Collagen/polysaccharide blends (e.g., 80/20, 50/50, 20/80%)(Chen et al., (2010) *Acta Biomaterialia* 6(2):372-82)

Electrospinning can be performed by any means known in the art (see, for example, U.S. Pat. No. 6,110,590). In certain aspects, a steel capillary tube with an internal diameter tip is mounted on an adjustable, electrically insulated stand. The capillary tube can be maintained at a high electric potential and mounted in the parallel plate geometry. The capillary tube can be connected to a syringe filled with a polymer solution. In certain aspects, a constant volume flow rate is maintained using a syringe pump, set to keep the solution at the lip of the tube without dripping. The electric potential, solution flow rate, and the distance between the capillary tip and the collection screen are adjusted so that a stable jet is obtained. Dry or wet fibers are collected by varying the distance between the capillary tip and the collection screen. Aligned fibers can be created using 1. a drum collection plate which rotates during electrospinning or 2. patterning the collection plate with conductive and non-conductive surfaces, allowing the fibers to align over the nonconductive area. In other embodiments a scaffold can be produced using three dimensional printing or freeze casting.

To generate nanofibers with diameters of 150-400 nm and a stiffness of 0.5, 0.75 to 1.0 MPa, including all values and ranges there between, for the promotion of myotube formation polymer solutions can be, but not limited to, electrospun at about 20-22 kV and about 20° C. and tune the flow rate and distance between spinneret and collector; as well as the ratio (viscosity) of polymer blends (food grade, NutriCargo) depending on the blend ratios and calcium carbonate concentration ($CaCO_3$), and D-glucono-delta-lacton (GDL). To ensure nanofibers are annealed to each other to form a solid scaffold the fibers can be crosslinked. In certain non-limiting aspects, additional calcium can be transiently added as needed post-collection for nanofiber crosslinking prior to cell seeding. In other aspects, particularly when using thermally crosslinked gel, one could use temperature (cooling) to crosslink fibers. In other aspects, glutaraldehyde vapor can be used to form crosslinks, e.g., when using gelatin as a scaffold component (Zhang et al., (2006) *Polymer* 47(8):2911-17). In other aspects genipin (extracted from gardenia fruit) can be used as a natural crosslinking agent (Bigi et al., (2002) *Biomaterials,* 23(24):4827-4832). In still other aspects, transglutaminase and 1-Ethyl-3-(3-dimethylaminopropyl)carbodiimide (EDC) can be used to crosslink fibers (Yang et al., (2018) *Scientific reports* 8(1):1616). In certain aspects, the nanofiber scaffold can be functionalized. In certain aspects, the functional moiety can be RGD peptide. Crosslinking densities can be optimized to achieve a gap spacing of 25 to 200 μm to allow for the injection of adipocytes. In certain aspects the gap spacing is about 100 μm. In certain aspects, cell-cell interactions assist in cross linking or substitutes in part or in whole for a cross-linking agent.

Physical properties of nanofiber scaffolds can be measured. In certain aspects, polymer(s) composition (e.g., pectin/alginate ratio), calcium concentration, applied voltage, and flow rate can be used to define the nanofiber scaffolds. The elastic modulus of nanofibers, which is critical for myocyte adhesion and differentiation, can be measured using an atomic force microscope (Ostrovidov et al., *J. Biomaterials.* 35, 6268-77, 2014; Nguyen et al., *Integrative Biol.* 8, 1232-45, 2016; Kim et al., *J Cell Sci.* 194803, 2016). To determine the average diameter of electrospun fibers and scaffold porosity, field emission scanning electron microscopy (FE-SEM) can be used and quantitative image analysis performed using MATLAB. The nanofiber scaffold architecture can be determined by measuring skeletal muscle or myotube formation: Light microscopy and quantitative image analysis can be used to measure: cell viability (propidium iodide); the length and aspect ratio of myotubes (Cell Tracker™, a fluorescent dye, ThermoFisher®); and the number of nuclei, which increases with myotube formation (DRAQ5,®, a far-red stain, Abcam®). Levels of skeletal muscle markers can be measured, including proteins (skeletal muscle myosin, MY-32, Abcam®) and transcripts, such as upregulation of early myoblast differentiation markers (Myogenic Factor 6, Myf6, MRF4) and terminal myotube markers (Myosin Heavy Chain, MHC) using RT-PCR (Olguin and Olwin, *Developmental Biol.* 275, 375-88, 2004; Mastroyiannopoulos et al., *PLOS One* 7, e29896, 2012).

In certain embodiments myocytes, e.g., bovine myocytes, can be isolated from fresh muscle and cultured in an appropriate medium under appropriate conditions. In certain aspects, the dimensions of the resultant cultured meat (as dictated by the heterogeneous scaffold) can be optimized to ensure gas and nutrient exchange during culture. In certain aspects the heterogeneous scaffold can be 0.1, 0.2, 0.3, 0.4, 0.5, 0.6, 0.7, 0.8, 0.9, 1 to 2 mm thick for culture purposes. In certain embodiments 1, 2, 3, 4, 5, 6, 7, 8, 9, 10 or more cultured heterogeneous scaffolds can be combined post-culture to for a product having a thickness of 1, 2, 3, 4, 5, 6, 7, 8, 9, 10, 11, 12, 13, 14, 15, 16, 17, 18, 19, to 20 mm or more. The heterogeneous scaffolds can be crosslinked as described above. Myocytes can be seeded at a density of 10, 100, 1000, $1\times10^4$, $1\times10^5$, $1\times10^6$ or more cells/$\mu m^2$, including all ranges and values there between. The seeded myocytes can be induced to form myotubes. In certain aspects, myotube formation is induced by serum-starvation.

The nanofibrous scaffold that successfully forms myotubes with spacing requirements for the injection of adipocyte-scaffolds will be used. Other approaches may be used to produce structured hydrogel scaffolds, such as 3D printing (Miri et al., 1800242, 2018) or freeze-casting (Riblett et al., *J Advanced Functional Materials* 22, 4920-23, 2012). The production of nanofibers can be tested using additional source ingredients that have low energy, water, land use, and GHGE impact, such as cellulose or agarose, at a density to recapitulate the optimal stiffness using formulations established for myotube formation. Additional scaffold compositions can be tested using the ranked list of ingredients that consumers find the most appealing. For example, if the concept of pectin recovered from citrus waste is found unappealing, one will consider other plant-based alternatives, such as alginate and agarose.

2. Secondary Scaffold

Figure 1:
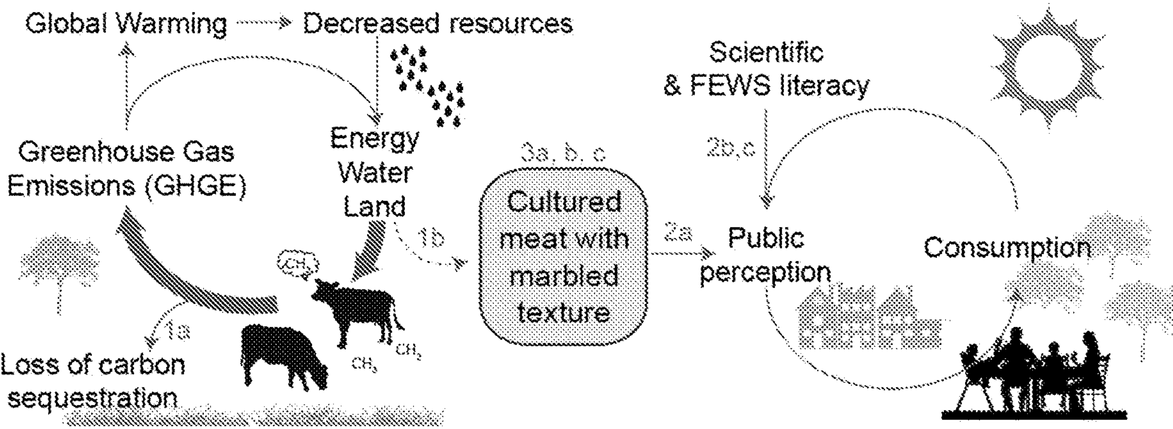
FIG. 1. Overview of the broad goals to be achieved by production of cultured meat products.
Figure 2:
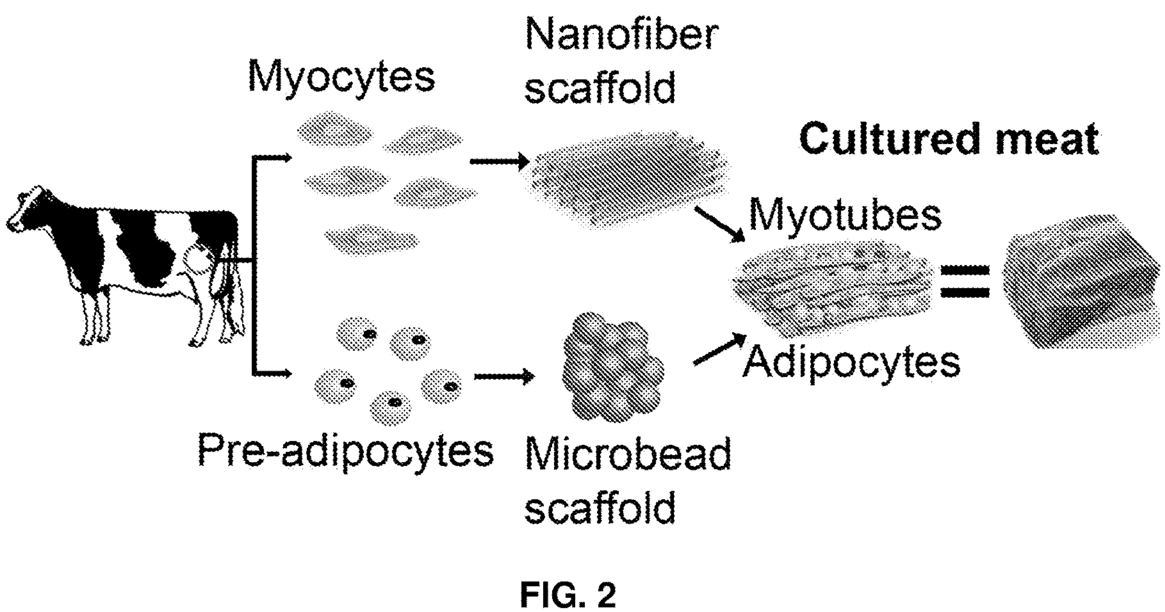
FIG. 2. Overview of a strategy for generation of heterogeneous scaffold using convergence of electrospinning and microbead technologies resulting in a cultured meat product.

In addition to a nanoporous scaffold, a heterogeneous scaffold comprises at least a second scaffold for supporting growth and/or development of adipocytes or other non-myocyte cell types (e.g., macrophages and/or other immune cells, tumor cells, fibroblasts, etc.). In certain aspects, the second scaffold is an adipocyte microcarrier scaffold. The adipocyte microcarrier scaffold has a first dimension between 50 to 500 μm and a second dimension of 50 to 500 μm. In certain aspects, the adipocyte microcarrier scaffold is spherical, ovoid, cylindrical, or egg shaped. In certain instances, the adipocyte microcarrier scaffold has an average aspect ratio (long axis to short axis) ranging from 1, 2, 3, 4, 5, 6, 7, 8, 9, to 10 including all ratios and ranges there between. Adipocytes can be integrated or injected into the myocyte/nanofiber scaffolds at 0.5, 1, 5, 10, 15, 20, 30, 40, 50, 60, 70, or 80% dry weight, including all values and ranges there between, of the total heterogeneous scaffold content, which can be ideal for beef texture and palatability (Frank et al., *Journal of agricultural and food chemistry* 64, 4299-4311, 2016). In certain aspects, fat, adipocytes and/or pre-adipocytes are integrated into the heterogeneous scaffold or muscle scaffold by injecting or integrating microgel particles into a nanoporous scaffold. Microgel particles can be fabricated that have stiffness of about 0.5, 1, 1.5, 2.0 to 2.5 kPa. Preferably about 2 kPa to promote maturation of pre-adipocytes. Other scaffolds or substrates can be used in place of microgel particles. For example, the pre-adipocyte/microgel slurry can be injected into the myocyte/nanofiber scaffold after myocytes have adhered to the nanofibers. In certain aspects partial crosslinking, e.g., with calcium ($CaCO_3$ and GDL), can be performed to stably link microgels to each other and to the nanofibers, forming an interconnected scaffold with regions of varying stiffness and cell types (FIG. 2). If adipocyte spatial distribution needs to be adjusted the microgels or adipocyte scaffold or substrate can be pre-seeded with pre-adipocytes to encourage adhesion before injection or integration. In certain aspects, a calcium-crosslinking can be used for cell encapsulation (Lee and Mooney, *J Progress in polymer science* 37, 106-26, 2012; Alborzi et al., *Journal of food science* 75, C100-C107, 2010; Sun and Tan, *J. Materials.* 6, 1285-1309, 2013), transient calcium is not anticipated to negatively impact cells. In other aspects, cell-cell interactions are sufficient for cross-linking one or more scaffold components.

Pre-adipocytes can be isolated from muscle or other tissues (Hausman and Poulos, *Journal of animal science* 83, 1010-16, 2005) and treated in skeletal muscle cell growth medium to prime them for co-culture with myocytes.

In certain aspects, gelatin microgels can be generated using water-in-oil emulsions. For example, a 1, 5, 10, 15, 20% gelatin (including all ranges and values there between) and 0, 1, 2, 3, 4, 5, 6, 7, 8, 9, 10% transglutaminase (including all ranges and values there between) can be mixed and emulsified in light mineral oil with 0.25, 0.5, 0.75, 1, 1.25, 1.5, 1.75, to 2% span 80 (including all ranges and values there between).

In other aspects, pectin-alginate microgel particles with stiffness ~2 kPa and final swollen diameter of 50-100 μm can be generated using microfluidic water-in-oil emulsions (Griffin et al., *Nature materials* 14, 737-744, 2015). Scaffolds containing both myocytes and adipocytes will be incubated at 37° C. in 5% $CO_2$ in media along with lipid inducing medium (Abbott et al., 5, 1667-77, 2016).

Successful co-culture or mixing cultured heterogeneous microcarriers will result in marbled, cultured meat, whose composition will be defined by the magnitude of mature myotubes and interspersed adipocytes and their fat content. To quantify the spatial patterning of fat, intracellular lipid droplets can be quantified using fluorescence imaging of Oil red O (ThermoFisher). To confirm that cells have committed to adipocyte formation expression of adipogenic markers C/EBPα and PPARγ can be measured using RT-PCR (Kim et al., *J Cell Sci.* 194803, 2016; Pan et al., 7, 25930, 2016). Myocyte organization will be determined using immunostaining.

In some embodiments, a food product or cultured meat described herein can further comprise one or more additional nutritional component or nutritional additive. The one or more additional nutritional component or nutritional additive can be present at about or at most 0.1%, 0.5%; 1.0%; 1.5%; 2.0%; 2.5%; 3.0%; 3.5%; 4.0%; 4.5%; 5.0%; 5.5%; 6.0%; 6.5%; 7.0%; 7.5%; 8.5%; 9.0%; or 9.5% by weight (w/w/ or weight percent). In some aspects, a food product or cultured meat described herein can further comprise one or more vitamins selected from Vitamin A, Vitamin D3, Vitamin E, Vitamin B12, Vitamin B2, Vitamin B6, Vitamin C, Vitamin K1, and combinations thereof. The types of Vitamin A can include, for example, palmitate; the types of Vitamin D3 can include, for example, cholecalciferol; the types of Vitamin E can include, for example, dl-alpha-tocopheryl acetate; the types of Vitamin B 12 can include, for example, cyanocobalamin; the types of Vitamin B2 can include, for example, riboflavin; the types of Vitamin B6 can include, for example, pyridoxine HCL; the types of Vitamin C can include, for example, ascorbic acid; the types of Vitamin K1 can include, for example, phytonadione.

In some embodiments, the food product or cultured meat described herein further comprises one or more minerals selected from potassium iodide (as a source of iodine), ferrous fumarate (as a source of iron), manganese sulfate (as a source of manganese), zinc sulfate (as a source of zinc), and combinations thereof.

The food product or cultured meat can comprise or further comprise additional protein of at least 7% protein, preferably at least 8% protein, more preferably at least 9% protein, more preferably at least 10% protein, most preferably at least 10.5% protein, such as 11% protein. The protein in food product or cultured meat can be any type of high quality protein, such as milk protein, whey, casein or soy protein, or a mixture thereof. In certain aspects, at least 4% to 50% of total protein consist of the amino acid leucine, preferably L-leucine.

The food product or cultured meat can comprise or further comprise at least one source of fat and at least one source of carbohydrates. The lipids making up the fat source may be any suitable fat or mixture fats, including animal fats, such as milk fat, and vegetable fats. In other aspects, the fat source can be a cell or a fat cell, the cell or fat cell can be genetically engineered to produce a specified molecular profile, e.g., fat, protein profile etc. Suitable vegetable fats are soy oil, palm oil, coconut oil, safflower oil, sunflower oil, corn oil, canola oil, and lecithins. Any suitable carbohydrates may be used, for example start, such as (modified) corn starch or potato starch, sucrose, lactose, glucose, fructose, corn syrup solids, and maltodextrins, and mixtures thereof.

The food product or cultured meat can comprise or further comprise dietary fibers. The food product or cultured meat can comprise or further comprise at least 7% protein, a source of fat and a source of carbohydrate preferably comprises at least 2 g fiber per 100 g of food product or cultured meat, more preferably at least 3 to 10 g per 100 g, more preferably at least 4 g per 100 g, more preferably at least 4.5 g per 100 g, more preferably at least 4.8 g per 100 g. The food product or cultured meat can comprise or further comprise between 2 and 10 g fiber per 100 g.

Many types of dietary fibers are suitable and available for use. Examples of suitable fibers include, but are not limited to, galactooligosaccharide, fructooligosaccharides, inulin, pectin, 6-glucans, gums such as gum arabic, tragacanth, mucilages, guar and locust bean gum, agar, carageenans, alginates, xanthan, pea fiber and soy fiber.

To tune the marbling of cultured beef the myocyte to adipocyte ratio can be varied to tune the cultured beef texture, flavor, and nutritional content. Fat content and marbling of a food product or cultured meat can be adjusted by varying the density of lipid producing adipocytes to comprise at least, at most, or about 0, 5, 10, 15, 20, 25, 30, 35, 40, 45, to 50% by mass of the total material. In certain aspects the myocyte to adipocyte ratio in the resulting food product is 10:1, 8:1, 6:1, 4:1, 2:1, 1:1 or any ratio there between. Texture, flavor and nutritional analyses results of marbled cultured meat will be compared to high quality standard beef (Wagyu) as well as pure myocyte-cultured meats.

Results from GC-MS will be compared to flavors found in steak such as 2-methylpropanal (brothy, meaty) and 3-methylbutanal (yeasty, salty, earthy)(Frank et al., *Journal of agricultural and food chemistry* 64, 4299-311, 2016). Nutritional analysis will be conducted by RL Food Testing Laboratory (Westlake Village, CA) to assess nutrient values (e.g., total calories, total carbohydrates, cholesterol, saturated fat, dietary fiber, iron, protein, sodium, sugars, and B12) of cultured meats. Nutritional information will be integrated into materials for dissemination.

EXAMPLES

The following examples as well as the figures are included to demonstrate non-limiting embodiments of the invention. It should be appreciated by those of skill in the art that the techniques disclosed in the examples or figures represent non-limiting techniques discovered by the inventors to function well in the practice of the invention. However, those of skill in the art should, in light of the present disclosure, appreciate that many changes can be made in the specific embodiments which are disclosed and still obtain a like or similar result without departing from the spirit and scope of the invention.

Example I

Generating Marbled Cultured Meat that has Desirable Texture and Flavor

Marbled cultured meat that meets the taste, texture, and nutritional profiles of beef produced in vivo. Methodology for generating materials with heterogeneous mechanical properties for co-culture of multiple cell types should be valuable for cultured meat production as well as in tissue engineering.

Establish structured scaffold to promote myotube formation. To form skeletal muscle that derives from bovine myocytes, a structured scaffold is generated from plant-based polymers such as pectin and alginate.

Cells: Bovine myocytes are isolated from fresh beef muscle (Hausman and Poulos, *Journal of animal science* 83, 1010-16, 2005) and cultured in Dulbecco's Modified Eagle Medium (DMEM) with 10% fetal bovine serum (FBS) and pH 6-8, which benefits meat texture and flavor (Calkins and Hodgen, A fresh look at meat flavor. 77, 63-80, 2007). In these proof-of-concept studies, 1% Penicillin/Streptomycin will be used as per standard cell culturing methods; since the presence of antibiotics in cultured meat is undesirable, future work will use sterile technique with no additional antibiotics.

Structured nanofibrous scaffold: To generate pectin-alginate nanofibers with diameters of 150-400 nm and stiffnesses of 0.5 to 1.0 MPa, for the promotion of myotube formation (Ostrovidov et al., *J applied materials & interfaces* 9, 42444-58, 2017; Choi et al., *J Biomaterials.* 29, 2899-2906, 2008; Ricotti et al., *J Biomedical materials* 7, 035010, 2012; Ostrovidov et al., *J. Biomaterials.* 35, 6268-77, 2014; Alborzi et al., *Journal of food science* 75, C100-C107, 2010), polymer solutions can be electrospun at 10-22 kV and 20° C. and tune the flow rate and distance between spinneret and collector; as well as the ratio (viscosity) of polymer blends (food grade, NutriCargo) depending on the blend ratios and calcium carbonate concentration ($CaCO_3$), and D-glucono-delta-lacton (GDL)(Alborzi et al., *Journal of food science* 75, C100-C107, 2010). To ensure nanofibers are annealed to each other to form a solid scaffold, additional calcium will be transiently added as needed post-collection for nanofiber crosslinking prior to seeding the cells. Myocyte adhesion can be enhanced by functionalizing the scaffold with RGD peptide (Rowley and Mooney, *Biomaterials.* 60, 217-23, 2002). For these proof-of-concept methods, the dimensions of the resultant cultured meat will be optimized to ensure gas and nutrient exchange. Bovine myocytes will be seeded at a density of 1,000 to 10,000 cells/$cm^2$, allowed to reach confluence for 3-5 days, serum-starved (2% FBS) to induce myotube formation, and observed after 2, 4, and 6 days. Crosslinking densities and electrospinning flow speed will be optimized to achieve a gap spacing of ~100 μm to allow for the injection of adipocytes. Alternatively, sheets of aligned nanofibers can be used to stack with layers of muscle cells on nanofibers, and adipocytes on beads.

Physical properties of nanofiber scaffolds can be measured as a function of pectin/alginate ratio, calcium concentration, applied voltage, and flow rate. The elastic modulus of nanofibers, which is critical for myocyte adhesion and differentiation (Levy-Mishali et al., *J Tissue Engineering Part A* 15, 935-44, 2009), can be measured using an atomic force microscope (Ostrovidov et al., *J. Biomaterials.* 35, 6268-77, 2014; Nguyen et al., *Integrative Biol.* 8, 1232-45, 2016; Kim et al., *J Cell Sci.* 194803, 2016). To determine the average diameter of electrospun fibers and scaffold porosity, field emission scanning electron microscopy (FE-SEM) can be used and quantitative image analysis performed using MATLAB. The nanofiber scaffold architecture can be determined by measuring skeletal muscle or myotube formation: Light microscopy and quantitative image analysis can be used to measure: cell viability (propidium iodide); the length and aspect ratio of myotubes (Cell Tracker™, ThermoFisher®); and the number of nuclei, which increases with myotube formation (DRAQ5®, Abcam®). Levels of skeletal muscle markers can be measured, including proteins (skeletal muscle myosin, MY-32, Abcam®) and transcripts, such as upregulation of early myoblast differentiation markers (Myogenic Factor 6, Myf6, MRF4) and terminal myotube markers (Myosin Heavy Chain, MHC) using RT-PCR (Olguin and Olwin, *Developmental Biol.* 275, 375-88, 2004; Mastroyiannopoulos et al., *PLOS One* 7, e29896, 2012).

Texture of cultured meat: Texture profile analysis can be conducted to define meat tenderness. Tensile properties will be quantified using an Instron Materials Testing Machine 5544 (Caine et al., *Meat science* 64, 333-39, 2003).

Statistical analyses: All experiments will be conducted at least three independent times to ensure reproducibility. Statistical significance between control and treated groups will be determined using unpaired t-test or one-way ANOVA with Tukey's multiple comparison post hoc analysis using a statistical software, GraphPad Prism® 5 (GraphPad® Software). Appropriate statistical methods will be used depending on the data collected; for example, electrospun scaffolds typically exhibit a non-normal distribution of pore sizes (Li et al., *Journal of Biomedical Materials Research* 60, 613-21, 2002), so Mann Whitney U tests will be used to determine statistical differences.

The nanofibrous scaffold that successfully forms myotubes with spacing requirements for the injection of adipocyte-scaffolds will be used. LCA will identify hotspots in the strategy that will provide targets for reductions in energy, water, land use, and GHGE. For example, if it is determined that electrospinning is a hotspot, other approaches to producing structured hydrogel scaffolds will be tested, such as 3D printing (Miri et al., 1800242, 2018) or freeze-casting (Riblett et al., *J Advanced Functional Materials* 22, 4920-23, 2012). The production of nanofibers can be tested using additional source ingredients that have low energy, water, land use, and GHGE impact, such as cellulose or agarose, at a density to recapitulate the optimal stiffness using formulations established for myotube formation. Additional scaffold compositions can be tested using the ranked list of ingredients that consumers find the most appealing. For example, if the concept of pectin recovered from citrus waste is found unappealing, one will consider other plant-based alternatives, such as alginate and agarose.

Certain embodiments are directed to methods for producing marbled cultured meat with myocytes and adipocytes. The methods can achieve marbled cultured meat where the content of interspersed fat cells between myotubes and can be tuned/optimized to produce cultured meat with improved texture and flavor compared to pure myocyte-cultured meat.

Adipocytes can be integrated into the myocyte/nanofiber scaffolds at 10-15% by mass of the total marbled scaffold content, which can be ideal for beef texture and palatability (Frank et al., *Journal of agricultural and food chemistry* 64, 4299-4311, 2016). To integrate fat into the muscle, MAPs microgel particles will be fabricated that have stiffness ~2 kPa to promote maturation of pre-adipocytes. The preadipocyte/microgel slurry will be injected into the myocyte/nanofiber scaffold on day 1 after myocytes have adhered to the nanofibers. In certain aspects partial crosslinking with calcium ($CaCO_3$ and GDL) can be performed to stably link microgels to each other and to the nanofibers, forming an interconnected scaffold with regions of varying stiffness and cell types (FIG. 2). If adipocyte spatial distribution needs to be adjusted the microgels can be pre-seeded with pre-adipocytes to encourage adhesion before delivering as a slurry. Calcium-crosslinking is routinely used for cell encapsulation (Lee and Mooney, *J Progress in polymer science* 37, 106-26, 2012; Alborzi et al., *Journal of food science* 75, C100-C107, 2010; Sun and Tan, *J. Materials.* 6, 1285-1309, 2013), transient calcium is not anticipated to negatively impact cells.

Cells: Pre-adipocytes will be isolated from bovine muscle (Hausman and Poulos, *Journal of animal science* 83, 1010-16, 2005) and treated in skeletal muscle cell growth medium for 24 h prior to co-culturing with myocytes in DMEM and FBS, following established protocol (Dietze et al., *Diabetes* 51, 2369-76, 2002); this will prime them for co-culture with myocytes. *MAPs*

Microgels: Pectin-alginate microgel particles with stiffness ~2 kPa and final swollen diameter of 50-100 μm will be generated using water-in-oil emulsions (Nybrerg et al., *Lab Chip* URL www.ibp.ucla.edu/research/rowat/Publications_files/Nyberg.LoC.2016.pdf; Nyberg et al., *Biophys J.* 113(7):1574-1584, 2017). Scaffolds containing both myocytes and adipocytes will be incubated at 37° C. in 5% $CO_2$ in media along with lipid inducing medium (Abbott et al., 5, 1667-77, 2016) and cells will be analyzed at 2, 4, and 6 days of incubation.

Analysis—Successful co-culture will result in marbled, cultured meat, whose composition will be defined by the magnitude of mature myotubes and interspersed adipocytes and their fat content. To quantify the spatial patterning of fat, intracellular lipid droplets can be quantified using fluorescence imaging of Oil red O (ThermoFisher). To confirm that cells have committed to adipocyte formation expression of adipogenic markers C/EBPα and PPARγ can be measured using RT-PCR (Kim et al., *J Cell Sci.* 194803, 2016; Pan et al., 7, 25930, 2016). Myocyte organization will be determined using immunostaining.

Experimental design will be guided by findings of LCA and surveys. For example, if it is determined that generating MAPs using microfluidic methods requires more energy than making emulsions for the scaffolds by parallel droplet generation (which requires lower pressure) or vortexing oil and water and subsequent size filtering, these alternative strategies can be tested.

Determining the texture, flavor, and nutritional content of cultured meat. To tune the marbling of cultured beef the myocyte to adipocyte ratio can be varied to tune the cultured beef texture, flavor, and nutritional content. Fat content and marbling of cultured meat can be adjusted by varying the density of lipid producing adipocytes to myocyte cells to comprise 0, 5, 10, 15, 20, and 25% by mass of the total material. Texture, flavor and nutritional analyses results of marbled cultured meat will be compared to high quality standard beef (Wagyu) as well as pure myocyte-cultured meats.

To quantify spatial heterogeneity and fat content, microtome sections of cultured meat will be imaged. AFM will be used to measure and map elastic modulus across the surface of the cultured meat using with a force probe tip with 5 μm diameter (Nguyen et al., *Integrative Biol.* 8, 1232-45, 2016;

Kim et al., *J Cell Sci.* 194803, 2016). To determine spatial organization of cells, spinning disk confocal microscope will be used, which is mounted on the AFM, to identify Cell Tracker-labeled myotubes and adipocytes by Oil Red O. Tensile properties of cultured meats with varying levels of fat will be measured. To measure flavor, compound analysis will be performed using Gas Chromatography Mass Spectrophotometry (GC-MS) (Molecular Instrumentation Center, UCLA).

Results from GC-MS will be compared to flavors found in steak such as 2-methylpropanal (brothy, meaty) and 3-methylbutanal (yeasty, salty, earthy)(Frank et al., *Journal of agricultural and food chemistry* 64, 4299-311, 2016). Nutritional analysis will be conducted by RL Food Testing Laboratory (Westlake Village, CA) to assess nutrient values (e.g., total calories, total carbohydrates, cholesterol, saturated fat, dietary fiber, iron, protein, sodium, sugars, and B12) of cultured meats. Nutritional information will be integrated into materials for dissemination.

Example 2

Figures 5A, 5B, 5C, 5D:
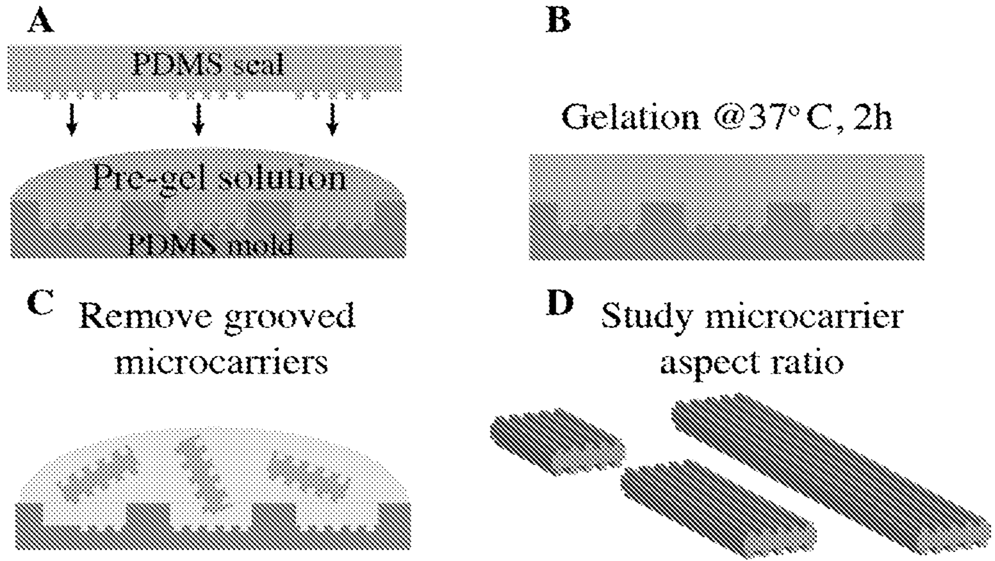
FIG. 5A-5D. Design of edible microcarrier scaffolds with tunable mechanics and surface topology. To create microcarrier scaffolds with aligned topology: (A) gelatin is cast into a PDMS mold with defined microgrooves and sealed with a grooved PDMS coverseal. (B) Gelation occurs for 2 hours in a cell culture incubator where the enzyme transglutaminase chemically crosslinks the gelatin. (C) After gelation, microcarrier scaffolds are removed from the mold, and can be prepared for cell culture in a spinning bioreactor. (D) Different shapes and aspect ratios of the microcarriers will be tested to optimize myotube alignment and differentiation.

Development of Microcarrier Scaffolds with Tunable Mechanics and Topology that are Compatible with Bioreacator Culture Generation of microcarrier scaffolds with tunable mechanics and topology to support myotubes. Microcarriers can be generated with tunable stiffness and aligned microgroove topology to support myotube maturation. Scaffolds will initially be fabricated using food-grade gelatin; this edible component is a key factor in the texture and mouthfeel of meat: with increased temperatures required for cooking, connective tissue (collagen) liquefies and degrades into gelatin which gives meat an unctuous mouthfeel. While gelatin is a solid at room temperature, it can be chemically crosslinked to provide structural support for mammalian cell culture at 37° C. To create edible microcarrier scaffolds, food grade transglutaminase can be used, which is an enzyme naturally found in mammalian cells that forms an isopeptide bond between glutamine and lysine amino acids, and has been used to crosslink gelatin hydrogels (Chambi and Grosso, *Food Research International* 39, 458-466, 2006). Using the transglutaminase-gelatin hydrogel system, gels with grooved topology have been produced by casting gelatin on a polydimethylsiloxane (PDMS) mold with defined 10 μm wide grooves that are 3 μm deep; cells seeded on these scaffolds exhibit alignment along the microgrooves (FIG. 5).

Figure 4:
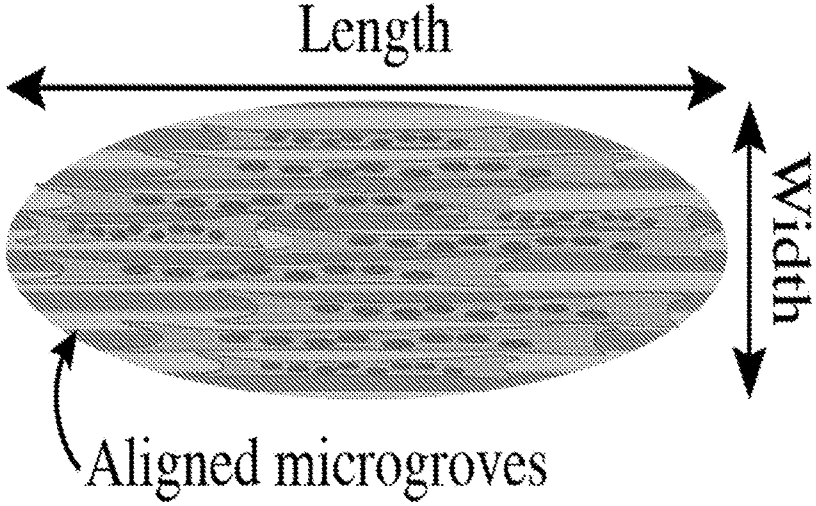
FIG. 4. Illustration of Myotube formation on microcarrier scaffolds with tunable mechanics and topology.

To determine the optimal the size, aspect ratio, and topology of microcarrier scaffolds for myotube differentiation (FIG. 4), printing methods include those similar to those described in the literature that build on inventor expertise in soft lithography (Yeh et al., *Biomaterials* 27, 5391-5398, 2006; Schmitz et al., Microfluidic device for storage and well-defined arrangement of droplets, 2009; Gill et al., *Lab on a Chip* 19, 343-357, 2019; Rowat et al., *Proc Natl Acad Sci USA* 106, 18149-18154, 2009; Merkel et al., *Proc Natl Acad Sci USA* 108, 586-591, 2011). The optimal stiffness for myocyte differentiation has been determined in the literature (Boonen et al., *Am J Physiol Cell Physiol* 296, C1338-1345, 2009; Engler et al., *J Cell Biol* 166, 877-887, 2004) and confirmed in preliminary experiments to be ~20 kPa. By modifying the concentration of both gelatin and transglutaminase, the stiffness of the resulting hydrogel will be modulated (Irvine et al., *Biomed Microdevices* 17, 16, 2015; Kim and Uyama, *Polym J* 39, 1040-1046, 2007). To determine how the aspect ratio of microcarriers impacts myotube differentiation, varying aspect ratios of oblong-shaped carrier particles from 1 to 10 will be assessed. Since grooved topologies promote myotube differentiation, the surface topology of the microcarrier particles will be varied to generate grooves with gap spacing between 5 μm and 40 μm. To identify the 'optimal' microcarrier scaffold properties, myocyte differentiation is assessed by quantifying myotube markers.

Develop tunable scaffolds to promote fat production by adipocytes. Data show that the differentiation of precursor mouse 3T3 adipocytes is sensitive to matrix stiffness, with adipocytes adhering and producing lipids on soft matrices of ~2 kPa. However, the fluid shear stresses cells are subject to in a bioreactor may impact cell-matrix interactions, differentiation efficiency, and ultimately fat production. To define optimal conditions for adipocyte culture and fat production in a single-batch bioreactor, microcarrier scaffolds for adipocytes are generated using emulsions as a template to generate food-grade gelatin hydrogel particles that are cross-linked using transglutaminase. Microcarrier stiffness will be tuned by varying the density of gelatin and crosslinker (transglutaminase) concentration. To quantify lipid production, fluorescent dyes such as LipidTOX™ Oil Red O and Nile Red can be used; as well as quantification of protein indicators of lipid production.

Defining the energy, water, land use, GHGE footprint for cultured meat scaffolds using LCA and estimate production cost. Life Cycle Assessment (LCA) and cost analysis can be used to assess proposed methods and source ingredients for cultured meat production using our microcarrier scaffolds. LCA can be used to quantify the production of beef per kilogram including direct and indirect inputs and outputs, from water needed for cattle food crops to methane produced by cows.

Gelatin is a desirable scaffolding material, as it derives naturally from collagen, an abundant protein of the extracellular matrix (ECM), to which mammalian cells naturally adhere. Gelatin is also a byproduct of the meat and fish industry, and therefore has a relatively low carbon footprint of 0.0437 kg $CO_2$/kg equivalent (Sampaio et al., *The International Journal of Life Cycle Assessment* 22, 767-783, 2017). Using LCA, the inventors can compare gelatin to plant-based source ingredients, which generally show promise for low environmental footprints. For example, pectin and alginate may be desirable scaffold materials (Roesijadi et al., Macroalgae as a biomass feedstock: a preliminary analysis. Pacific Northwest National Lab, Richland, WA, USA, 2010; Ozkan et al., *J Energy Conversion Management* 45, 1821-1830, 2004); previous studies show these scaffolds are mechanically tunable for cell-type specific growth by varying calcium ion concentration (Levesque-Tremblay et al., *J Planta* 242, 791-811, 2015). Importantly pectin and alginate are biocompatible and have similar physical properties as components of the ECM of mammalian tissues, which provide a scaffold for the growth of cells (Seymour et al., *Pectins and their manipulation*, Taylor & Francis, 2002; Ruvinov and Cohen, in *Biomaterials from Nature for Advanced Devices and Therapies* (eds N M Neves & R L Reis) 274, Wiley, 2016).

An outcome of LCA is to quantify the effect of changes in process, such as switching to electricity derived from solar panels to sustain cell cultures, which will enable improvement of energy use efficiency in cultured meat production. LCA will identify source ingredients and processes that have minimal energy, water, land use, and GHGE footprints. Different experimental processes will also be tested. The strategy is to fabricate microcarrier scaffolds using microfabrication printing methods in conjunction with comparing the energy, water, land use, and GHGE footprint of using 3D printing. Findings will also be compared to conventional production of beef and plant-based meats (Heller and Keoleian, Beyond Meat's Beyond Burger Life Cycle Assessment: A detailed comparison between a plant-based and an animal-based protein source. 1-38 (University of Michigan, Ann Arbor, 2018).

Develop composite structures fusing myotube and adipocyte microcarriers and determine effects of marbling on cultured meat texture. To obtain 10-25% fat content, which is ideal for beef texture and palatability (Frank et al., *Journal of agricultural and food chemistry* 64, 4299-4311, 2016), composite myotube-adipocyte scaffolds are generated. The fat content of the cultured meat will vary by varying the density of lipid-producing adipocytes on scaffolds to myotube scaffolds to comprise 0, 5, 10, 15, 20, and 25% by mass of the total material. To define the texture of marbled cultured meat with varying levels of fat, a texture profile analysis can be conducted, which is important to define meat 'tenderness'. The content of intramuscular fat in cultured meat in relation to its texture can be established.

Determine effects of marbling on cultured meat flavor and nutrient profile. Many desirable flavors and colors arise during the cooking of raw meat, specifically due to Maillard reactions: thermal oxidation of molecules create desirable "meaty" flavors, such as 2-methylpropanal (brothy, meaty) and 3-methylbutanal (yeasty, salty, earthy)(Frank et al., *Journal of agricultural and food chemistry* 64, 4299-4311, 2016; Bailey, in *The Maillard Reaction in Foods and Nutrition* (eds G. R. Waller & M. S. Feather) 1983). Many key flavor molecules derive from intramuscular fat, which has a high degree of unsaturated phospholipids; this makes marbling an important contributor to meat flavor and nutritional properties (Troy et al., *Korean J Food Sci Anim Resour* 36, 577-582, 2016). For example, unsaturated phospholipids in intramuscular fat contain linoleic acid and arachidonic acid, which upon cooking oxidize to produce key flavor and aroma compounds such as 2-nonenal (grassy), 2,4-decadienal (fatty), as well as trans-4,5-epoxy-(E)-2-decenal (metallic) and 1-octen-3-one (metallic)(Elmore et al., *J Agric Food Chem* 47, 1619-1625, 1999; Arshad et al., *Lipids Health Dis* 17, 223, 2018; Hornstein and Crowe, *J Agric Food Chem* 8, 494-498, 1960; Miller, Beef flavor: a white paper. (National Cattlemen's Beef Association, Centennial, CO 2001). Concentrations of key flavor and aroma compounds can be measured in both raw and cooked marbled cultured meat samples using Gas Chromatography Mass Spectrophotometry (GC-MS). To assess nutrient profile, total calories, carbohydrates, protein, cholesterol, saturated and unsaturated fat, dietary fiber, iron, sodium, sugars, and B12 can be assessed.

A. Methods

Cells: To establish proof-of-concept, C2C12 mouse myocytes and primary Rabbit Skeletal Muscle Cells (RbSkMC) will be used (Cell Applications). Bovine myocytes can be isolated from fresh beef muscle obtained from Corona Cattle Slaughterhouse (Corona, California)(Hindi et al., *Bio Protoc* 7, 2017) and cultured in Dulbecco's Modified Eagle Medium (DMEM) with 10% fetal bovine serum (FBS) and pH 6-8. 1% Penicillin/Streptomycin can be used as per standard cell culturing methods; since the presence of antibiotics in cultured meat is undesirable, future work will use sterile technique with no additional antibiotics.

Structured microcarrier scaffold: To generate microcarrier scaffolds with stiffness of ~20 kPa, PDMS elastomeric molds with specified microgroove geometry can be generated using a 'master' silicon wafer patterned with a SU-8 photoresist. A pre-polymer solution of gelatin and transglutaminase will be cast into the PDMS mold and overlaid with a PDMS seal that also contains a specified microgroove topology. Gelatin microcarriers will be crosslinked at 37° C. for 2 hours. After gelation, the PDMS seal will be removed and microcarriers hydrated, which will enable them to swell and be removed from the PDMS mold. Gelatin microcarriers will be collected and concentrated by centrifugation, enabling rapid and high-throughput production of microcarriers with specified geometry and topology.

Culturing cells on microcarrier scaffolds: Myocytes will be seeded on microcarriers at a density of $1\times10^5$ cells/m$^2$, serum-starved (2% FBS) after 1 day to induce myotube formation, and cultured in a 100 mL spinner flask at 60 RPM, 37° C. The optimal cell seeding density per density of microcarriers can be determined to define the optimal conditions for cell adhesion and proliferation.

To optimize fat production by adipocytes spherical microcarrier scaffolds with ~2 kPa stiffness to promote adhesion to microcarriers can be engineered.

Cells: To establish proof-of-concept growth and differentiation of pre-adipocytes on microcarriers, mouse 3T3-L1 preadipocytes can be used. Primary rabbit subcutaneous preadipocytes (Cloud Clone) and bovine white preadipocytes isolated from fresh beef muscle can also be assessed.

Microcarrier scaffolds for adipocytes: Spherical gelatin microcarriers with stiffness ~2 kPa and final swollen diameter of 50-100 μm can be generated using water-in-oil emulsions, as previously described (Nyberg et al., *Lab on a Chip* 16, 3330-3339, 2016). Adipocytes can be seeded on microcarriers at a density of $1\times10^5$ cells/μm$^2$ and cultured in a 100 mL spinner flask at 60 RPM, 37° C. for ~5 days to reach confluence, followed by 3 days in differentiation media.

Quantifying fat production: Intracellular lipid droplets can be quantified with Oil Red O (ThermoFisher®) and LipidTOX™ (ThermoFisher®). To confirm differentiation into adipocytes, expression of adipogenic markers C/EBPα and PPARγ using RT-PCR can be assessed.

Life Cycle Assessment. LCA will involve the following major steps: (a) Defining the system boundary: A preliminary system boundary for the study includes key elements such as the production and processing of source ingredients, the cattle needed as source of bovine cells, as well as inputs (water, electricity) for producing scaffolds and culturing cells (media, serum, etc.). All scaffold processing, and cell maturation inputs and outputs will be determined in terms of energy, water, land use, and GHGE from primary literature. (b) Collecting data: Primary data on energy, water and materials for protein production will be determined based on experimental methods. Secondary data on the resources and emissions associated with production of inputs to experiments will be obtained from peer-reviewed articles and government reports. Conservative values will be used. (c) Estimating life cycle indicators, cost of production, and sensitivity analyses: The sensitivity of estimates to variability and uncertainty in key determinants of each different dimension of environmental impact as well as cost will be assessed. Some potential examples for sensitivity include the environmental footprint of the electricity used for production and the technical efficiency of the process. The potential effects of scaling up production on the environmental footprint and cost can also be estimated. Since new technologies typically benefit from learning-by-doing and how costs scale with volume varies between industries, different assumptions about learning rates and scale economies can be tested.

To integrate fat into cultured meat, the adipocyte- and myotube-microcarriers will be seeded together to form a composite structure.

Cells: Differentiated adipocytes on microbeads will be combined with differentiated myotubes on grooved microcarriers. Initially test can be conducted to established mouse and rabbit cell lines, and then with cells isolated from bovine muscle (Hausman and Poulos, *Journal of animal science* 83, 1010-1016, 2005). Composite adipocyte-myotube structures—in other words, marbled cultured meat—will be incubated at 37° C. in 5% $CO_2$ in DMEM with 20% FBS media; initial studies show these conditions have no adverse effects on differentiated myotubes. The marbled cultured meat will be analyzed at 2, 4, and 6 days, comparing the properties of raw and cooked 1 cm circular samples of cultured meat samples (~1.5 mm thick). Tensile properties can be quantified using an Instron Materials Testing Machine 5544 (Caine et al., Meat science 64, 333-339, 2003). Spatial heterogeneity and fat content can be quantified by imaging microtome sections of cultured meat. To determine the spatial organization of cells, a spinning disk confocal microscope can be used, which is mounted on the AFM, to identify Cell Tracker-labeled myotubes and adipocytes by Oil Red O.

To determine the effects of marbling on flavor and nutrient profiles of cultured meat, the myocyte to adipocyte ratio can be varied and flavor compounds of raw and cooked samples measured using Gas Chromatography Mass Spectrophotometry (GC-MS) (Molecular Instrumentation Center, UCLA). Results from GC-MS can be compared to flavor compounds in beef, such as deca-2,4-dienal and trans-4,5-epoxy-(E)-2-decenal (Hornstein and Crowe, *J Agric Food Chem* 8, 494-498, 1960), and lean beef, such as 2-methylpropanal (brothy, meaty) and 3-methylbutanal (yeasty, salty, earthy) (Frank et al., *Journal of agricultural and food chemistry* 64, 4299-4311, 2016). Nutritional analysis can be conducted by RL Food Testing Laboratory (Westlake Village, CA) to assess nutrient values (e.g., total calories, total carbohydrates, cholesterol, saturated fat, dietary fiber, iron, protein, sodium, sugars, and B12) of cultured meats.

B. Results

Findings can identify optimal scaffold microcarrier architecture to promote myotube differentiation and lipid production by adipocytes. It is anticipated that shear stresses due to rotation in the spinner flask cell culture system may reduce cell adhesion and limit myotube differentiation and adipocyte adhesion, so there will be an optimal moderate spinner rotation speed for each cell-microcarrier pair. It is contemplated that microcarriers with oblong shape (high aspect ratio) will best accommodate the production of myotubes (precursor muscle fibers), but that particles that are too large may sediment. The optimal scaffold microcarrier size and stiffness for fat production by adipocytes can be defined. Since fluid shear stresses may inhibit fat production by adipocytes (Choi et al., *Cell Biochemistry and Biophysics* 75, 87-94, 2017), rotation that is too slow may result in increased aggregation and sedimentation of adipocytes scaffolds. Successful co-culture will result in marbled, cultured meat, whose composition can be defined by the magnitude of mature myotubes and interspersed adipocytes and their fat content. It is anticipated that a higher content of adipocytes will result in cultured meat with more tender texture, higher levels of desirable flavor compounds in cooked samples, as well as higher levels of unsaturated fats.

Physical properties of microcarrier scaffolds will be measured as a function of gelatin/transglutaminase ratio, size, and aspect ratio. The elastic modulus of microcarriers, which is critical for myocyte adhesion and differentiation (Levy-Mishali et al., *J Tissue Engineering Part A* 15, 935-944, 2009), can be measured using an atomic force microscope (J P K Nanowizard 4 AFM), as previously described (Kim et al., *J Cell Sci* 129, 4563-4575, 2016; Nguyen et al., Stiffness of pancreatic cancer cells is associated with increased invasive potential. 8, 1232-1245, 2016). To image the scaffold topology, emission scanning electron microscopy (FE-SEM) can be used and perform quantitative image analysis using MATLAB. The 'optimal' microcarrier scaffold architecture will be determined by measuring skeletal muscle or myotube formation: light microscopy can be used and quantitative image analysis to measure: cell viability (propidium iodide); the length and aspect ratio of myotubes (Cell Tracker™, ThermoFisher®); and the number of nuclei, which increases with myotube formation (DRAQ5®, Abcam®). Levels of skeletal muscle markers can be measured, including proteins (skeletal muscle myosin, MY-32, Abcam®) and transcripts, such as upregulation of early myoblast differentiation markers (Myogenic Factor 6, Myf6, MRF4) (Verbruggen et al., *Cytotechnology* 70, 503-512, 2018) and terminal myotube markers (Myosin Heavy Chain, MHC2B) using RT-PCR, as previously described (Olguin and Olwin, *J Developmental biology* 275, 375-388, 2004; Mastroyiannopoulos et al., *PloS one* 7 e29896, 2012)

Statistical analyses: All experiments will be conducted at least three independent times to ensure reproducibility. Statistical significance between control and treated groups will be determined using unpaired t-test or one-way ANOVA with Tukey's multiple comparison post hoc analysis using GraphPad Prism® 5 (GraphPad® Software). Appropriate statistical methods are used depending on the data collected; for example, Mann Whitney U tests will be used to determine statistical differences between non-normally distributed data sets.

Quantification of adipocyte behavior and lipid production: Over the 3-7 days of differentiation, adipocyte size and morphology can be measured at regular intervals, which are important indicators of cell-microcarrier adhesion. Since the inventors have found that cells and microcarriers tend to aggregate in culture due to cell-cell and cell-matrix adhesions, the size of clusters can be monitored during culture. To quantify lipid production, target genes for PPAR gamma CD36 and fatty acid synthase (FAS) will be assayed using RT-PCR. Lipid levels will be quantified over a range of microcarrier scaffold size and stiffness, as well as spinner flask RPM.

Life cycle energy, water, land, and GHGE can be compared for all inputs per kg of beef produced. Since cultured meat, conventional beef, and plant-based meat, may have different protein contents, outputs can be normalized per g protein per kg beef. Findings for conventional beef and other methods for producing cultured meat or plant-based burgers will be compared to the literature (Opio et al., *A global life cycle assessment* 1-214, 2013; Pelletier et al., *Agri Systems* 103, 380-389, 2010; Bryngelsson et al., *Food Policy* 59, 152-164, 2016).

Texture, flavor, and nutrient analyses of the marbled cultured meat will be determined as a function of % fat/weight compared to high quality standard beef (Wagyu) as well as pure myocyte-cultured meats.

The invention claimed is:

1. A cultured food product comprising a mixture of:

a first microcarrier scaffold containing myocytes; and a second microcarrier scaffold containing adipocytes, and wherein myocytes and adipocytes in the cultured food product are at a ratio between 20:1 to 2:1 and wherein the first microcarrier scaffold has a nanofiber component that is an aligned nanofiber component comprising aligned nanofibers.

2. The cultured food product of claim 1, wherein the first microcarrier scaffold comprises grooves having a length of 50 to 500 μm, depth of 1 to 50 μm and a width of 1 to 50 μm with a spacing between grooves of 1 to 50 μm.

3. The cultured food product of claim 1, wherein the first microcarrier scaffold has a first dimension between 50 to 500 μm and a second dimension of 50 to 500 μm, wherein the first microcarrier scaffold is spherical, ovoid, cylindrical, or egg shaped.

4. The cultured food product of claim 1, wherein the second microcarrier scaffold has a first dimension between 50 to 500 μm and a second dimension of 50 to 500 μm, wherein the adipocyte microcarrier scaffold is spherical, ovoid, cylindrical, or egg shaped.

5. The cultured food product of claim 1, wherein the aligned nanofibers are functionalized.

6. The cultured food product of claim 1, wherein the aligned nanofibers are RGD functionalized.

7. The cultured food product of claim 1, wherein the aligned nanofibers have a diameter of 150 to 400 nm.

8. The cultured food product of claim 1, wherein the first microcarrier-scaffold comprises patterned aligned stripes with gaps of 3 μm to 40 μm.

9. The cultured food product of claim 1, wherein the first or second microcarrier scaffold comprises pectin, alginate, agarose, elastin, chitin, chitosan, fibrin, fibrinogen, polysaccharides, alginates, collagen, gelatin, poly(amino acids), peptides, polypeptides, poly(a-hydroxyacids), polylactic or polyglycolic acids, poly-lactide poly-glycolide copolymers, poly-lactide polyethylene glycol (PEG) copolymers, polyesters, poly(ε-caprolactone), poly(3-hydroxy-butyrate), poly (s-caproic acid), poly(p-dioxanone), poly(propylene fumarate), poly(ortho esters), polyol/diketene acetal addition polymers, polyanhydrides, poly(sebacic anhydride) (PSA), poly(carboxybiscarboxyphenoxyphenoxyhexane) (PCPP), poly[bis(p-carboxyphenoxy)methane] (PCPM), copolymers of SA, CPP and CPM poly(amino acids), poly (pseudo amino acids), polyphosphazenes, derivatives of poly[(dichloro)phosphazene], poly[(organo)phosph-azenes] polymers, polyphosphates, polyethylene glycol polypropylene block co-polymers, co-polymers prepared from the monomers of these polymers, random blends of these polymers, or mixtures and combinations thereof.

10. The cultured food product of claim 1, wherein the first microcarrier scaffold is crosslinked.

11. The cultured food product of claim 1, wherein the first or second microcarrier scaffold comprises gelatin, pectin, alginate, agarose, or mixtures thereof.

12. The cultured food product of claim 1, wherein the myocytes are mammalian, avian, or fish myocytes.

13. The cultured food product of claim 12, wherein the mammalian myocytes are cow, pig, sheep, rabbit, fish, goat, deer, elk, or bison myocytes.

14. The cultured food product of claim 1, wherein the adipocytes are mammalian, avian, or fish adipocytes.

15. The cultured food product of claim 14, wherein the mammalian adipocytes are cow, pig, sheep, rabbit, fish, goat, deer, elk, or bison adipocytes.

16. The cultured food product of claim 1, wherein the myocytes are from the same species as the adipocytes.

17. The cultured food product of claim 1, wherein the myocytes are from a different species than the adipocytes.

18. The food product of claim 1, wherein the ratio of myocytes to adipocytes is 10:1 to 2:1.

19. The cultured food product of claim 1, wherein the food product contains 5 to 80 weight percent myotubes or myocyte substitute.

20. The cultured food product of claim 1, wherein the food product contains 0.5 to 50 weight percent adipocytes or adipocyte substitute.

21. The cultured food product of claim 1, further comprising additional nutritional components, wherein the additional nutritional components are vitamins, minerals, polysaccharides, lipids, proteins, polypeptides, peptides, or dietary fiber.

* * * * *